US005914266A

United States Patent [19]
Randazzo

[11] Patent Number: 5,914,266
[45] Date of Patent: Jun. 22, 1999

[54] MAMMALLIAN SEX COMB ON MIDLEG (MAMMALIAN SCM) ACTS AS A TUMOR SUPPRESSOR

[75] Inventor: Filippo Randazzo, Emeryville, Calif.

[73] Assignee: Chiron Corporation, Emeryville, Calif.

[21] Appl. No.: 08/852,153

[22] Filed: May 6, 1997

[51] Int. Cl.$^6$ ........................... C12N 15/00; C07H 21/02
[52] U.S. Cl. ...................................... 435/320.1; 536/23.1
[58] Field of Search .................................. 536/24.1, 23.1; 435/320.1

[56] References Cited

PUBLICATIONS

Sato et al., "Homoeosis in Drosophia: A New Enhancer of Polycomb and Related Homoeotic Mutations" *Genetics* 105:357–370, Oct. 1983.

Kennison and Tamkun, "Dosage–Dependent Modifiers of Polycomb and Antennapedia Mutations in Drosphila" *Proc. Natl. Acad. Sci. USA* 85:8136–8140, Nov. 1988.

Lewin, "Commitment and Activation at Pol II Promoters: A Tail of Protein—Protein Interactions" *Cell* 61:1161–1164, Jun., 1990.

Paro, "Imprinting a Determined State into the Chromatin of Drosophila" *TIG* 6 (20):416–421, Dec., 1990.

Goebl, "The bmi–1 and mel–18 Gene Products Define a New Family of DNA–Binding Proteins Involved in Cell Proliferation and Tumorigenesis" *Cell* 66:623, Aug., 1991.

Brunk et al., "Drosophila Genes Posterior Sex Combs and Suppressor Two of Zeste Encode Proteins With Homology to the Murine bmi–1 Oncogene" *Nature* 353:351–353, Sep., 1991.

van Lohuizen et al., "Sequence Similarity Between the Mammalian bmi–1 Proto–Oncogene and the Drosophila Regulatory Genes Psc and Su(z)2" *Nature* 353:353–355, Sep., 1991.

DeCamillis et al., "The Polyhomeotic Gene of Drosophila Encodes a Chromatin Protein that Shares Polytene Chromsome–Binding Sites with Polycomb" *Genes and Development* 6:223–232, 1992.

Felsenfeld, "Chromatin as an Essential Part of the Transcriptional Mechanism"*Nature* 355:219–224, Jan., 1992.

Sinclair et al., "Genetic Analysis of the Additional Sex Combs Locus of Drosophila Melanogaster" *Genetics* 130:817–825, Apr., 1992.

Travers, "The Reprogramming of Transcriptional Competence" *Cell* 69:573–575, May, 1992.

Djabali et al., "A Trithorax–Like Gene is Interrupted by Chromosome 11q23 Translocations in Acute Leukaemias" *Nature Genetics* 2:113–118, Oct., 1992.

Gu et al., "The t(4;11) Chromosome Translocation of Human Acute Leukemias Fuses the All–1 Gene, Related to Drosophila trithorax, to the AF–4 Gene" *Cell* 71:701–708, Nov., 1992.

Tkachuk et al., "Involvement of a Homolog of Drosophila Trithorax by 11q23 Chromsomal Translocations in Acute Leukemias" *Cell* 71:691–700, Nov., 1992.

Winston and Carlson, "Yeast SNF/SWI Transcriptional Activators and the SPT/SIN Chromatin Connection" *TIG* 8(11):387–391, Nov., 1992.

Barba et al., "Hox Gene Expression in Human Cancers" *Advances in Nutrition and Cancer* pp. 45–57, 1993.

Cillo, "Hox Genes in Human Cancers" *Invasion Metastasis* 14:38–49, 1994–1995.

Moehrle and Paro, "Spreading the Silence: Epigenetic Transcriptional Regulation During Drosophila Development" *Developmental Genetics* 15:478–484, 1994.

Kennison, "Transcriptional Activation of Drosophila Homeotic Genes from Distant Regulatory Elements" *TIG* 9(3):75–79, Mar., 1993.

van deg Lugt et al., "Posterior Transformation, Neurological Abnormalities, and Severe Hematopoietic Defects in Mice with a Targeted Deletion of the bmi–1 proto–oncogene" *Genes and Development* 8:757–769, 1994.

Denis and Green, "A Novel, Mitogen–Activated Nuclear Kinase is Related to a Drosophila Development Regulator" *Genes and Development* 10:261–271, 1996.

Epstein, "Polycomb and Friends" *BioEssays* 14(6):411–413, 1992.

Chiba et al., "Two Human Homologues of *Saccharomyces cerevisiae* SW12/SNF2 and *Drosophila brahma* are Transcriptional Coactivators Cooperating with the Estrogen Receptor and the Retinoic Acid Receptor" *Nucleic Acids Research* 22(10):1815–1820, 1994.

Nomura et al., "Isolation and Characterization of Retinoic Acid–Inducible cDNA Clones in F9 Cells: One of the Early Inducible Clones Encodes a Novel Protein Sharing Several Highly Homologous Regions with a Drosophila polyhomeotic Protein" *Differentiation* 57:39–50, 1994.

Watson et al., "Drosophila in Cancer Research: the First Fifty Tumor Suppressor Genes" *J. Cell Science* 18:19–33, 1994.

Kanno et al., "mel–18, a Polycomb Group–Related Mammalian Gene, Encodes a Transcriptional Negative Regulator With Tumor Suppressive Activity" *The EMBO Journal* 14(22):5672–5678, 1995.

(List continued on next page.)

*Primary Examiner*—Paula K. Hutzell
*Assistant Examiner*—Lin Sun-Hoffman
*Attorney, Agent, or Firm*—Banner & Witcoff; Jane E. R. Potter; Robert P. Blackburn

[57] ABSTRACT

Mammalian Scm gene and amino acid sequences encoded by the mammalian Scm gene, are described. The mammalian Scm gene and gene products are useful for diagnostic and therapeutic applications in proliferative and developmental disorders. Modulators of mammalian Scm can be identified using the dislcosed genes. The modulators can be used in the context of cancer therapy or a treatment of a developmental disorder. Scm is also useful for inducing differentiation in a population of progenitor cells.

4 Claims, No Drawings

PUBLICATIONS

Santamaria and Randsholt, "Characterization of a Region of the X Chromosome of Drosophila Including multi sex combs (mxc), a Polycomb Group Gene which also Functions as a Tumour Suppressor" *Mol. Gen. Genet.* 246:282–290, 1995.

Pirrotta, "Chromatin Complexes Regulating Gene Expression in Drosophila" *Current Opinion in Genetics and Development* 5:466–472, 1995.

Stuart et al., "PAX and HOX in Neoplasia" *Advances in Genetics* 33:255–274, 1995.

Tamkun, "The Role of Brahma and Related Proteins in Transcription and Development" *Current Opinion in Genetics and Dvelopment* 5:473–477, 1995.

Yu et al., "Altered Hox Expression and Segmental Identify in MII–mutant Mice" *Nature* 378:505–508, Nov. 1995.

Chang et al., "Interactions of polyhomeotic with Polycomb Group Genes of Drosophila melanogaster" *Genetics* 138:1151–1162, Dec., 1994.

Soto et al., "Comparison of Germline Mosaics of Genes in the Polycomb Group of Drosophila melanogaster" *Genetics* 140:231–243, May, 1995.

EST accession number HUM131E05B Dec. 1995.

Adams et al, Human brain Expressed Sequence Tag EST00767, ID Q59800 standard.

Hillier et al, WashU–Merck EST Project. Locus T69104.

Marra et al, The WashU–HHMI Mouse EST Project. ID: MM7255.

Hillier et al, The WashU–Merck EST Project. Locus W04698.

Watson et al. Recombinant DNA, 2nd, Scientific American Books, 1992.

Stratagene Catalog, p. 16.

Adams et al., "Initial of human gene diversity and expression patterns based upon 52 million basepairs of cDNA sequence", GenBank Accession Number T34096.

Hillier et al., "The WashU–Merck EST project", Genbank Accession Number R19817.

Yoshida et al., "Structure and expression of two highly related genes encoding SCM–1/human lymphotactin", FEBS lett. 395(1):82–8.

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
        (A) LENGTH: 2855 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

```
CAAATCATAA TAATGCAGGT CATTTTACCT GGGACAAATA CCTAAAAGAA ACATGTTCAG      60

TCCCAGCGCC TGTCCATTGC TTCAAGCAGT CCTACACACC TCCAAGCAAC GAGTTCAAGA     120

TCAGTATGAA ATTGGAAGCA CAGGACCCCA GGAACACCAC ATCCACCTGT ATTGCCACAG     180

TAGTTGGACT GACAGGTGCC CGCCTTCGCC TGCGCCTTGA TGGGAGCGAC AACAAAAATG     240

ACTTCTGGCG GCTGGTTGAC TCAGCTGAAA TCCAGCCTAT TGGGAACTGT GAAAAGAATG     300

GGGGTATGCT ACAGCCACCT CTTGGATTTC GGCTGAATGC GTCTTCTTGG CCCATGTTCC     360

TTTTGAAGAC GCTAAATGGA GCAGAGATGG CTCCCATCAG GATTTTCCAC AAGGAGCCAC     420

CATCGCCTTC CCACAACTTC TTCAAAATGG GAATGAAGCT AGAAGCTGTG GACAGGAAGA     480

ACCCTCATTT CATTTGCCCA GCCACTATTG GGGAGGTTCG GGGCTCAGAG GTGCTTGTCA     540

CTTTTGATGG GTGGCGAGGG GCCTTTGACT ACTGGTGCCG CTTCGACTCC CGAGACATCT     600

TCCCTGTGGG CTGGTGTTCC TTGACTGGAG ACAACCTGCA GCCTCCTGGC ACCAAAGTTG     660

TGATTCCAAA GAATCCCTAT CCTGCCTCCG ATGTGAATAC TGAGAAGCCC AGCATCCACA     720

GCAGCACCAA AACTGTCTTG GAACATCAAC CAGGGCAGAG GGGGCGTAAA CCAGGAAAGA     780

AGCGGGGCCG GACACCCAAG ACCCTAATTT CCCATCCCAT CTCTGCCCCA TCCAAGACAG     840
```

```
CTGAACCTTT GAAATTCCCA AAGAAGAGAG GTCCCAAACC TGGCAGCAAG AGGAAACCTC      900

GGACTTTGCT GAACCCACCA CCTGCCTCAC CAACAACCAG CACTCCTGAA CCGGATACCA      960

GCACTGTACC CCAGGATGCT GCCACCATCC CCAGCTCAGC CATGCAGGCC CAACAGTTTT     1020

GTATCTACTT GAACAAGAAT GGCAGCACAG GCCCCCACTT AGATAAGAAG AAGGTCCAGC     1080

AACTCCCTGA CCATTTTGGA CCAGCCCGTG CCTCTGTGGT GTTGCAGCAG GCTGTCCAGG     1140

CCTGTATCGA CTGTGCTTAT CACCAGAAAA CCGTCTTCAG CTTCCTCAAG CAAGGCCATG     1200

GTGGTGAGGT TATCTCAGCC GTGTTTGACC GGGAACAGCA TACCCTCAAC CTCCCAGCAG     1260

TCAACAGCAT CACCTACGTC CTCCGCTTCC TGGAGAAACT CTGCCACAAC CTTCGTAGTG     1320

ACAATCTGTT TGGCAACCAG CCCTTTACAC AGACTCACTT GTCACTCACT GCCATAGAGT     1380

ACAGCCACAG CCACGACAGG TACCTACCAG GTGAAACCTT TGTCCTGGGG AATAGTCTGG     1440

CCCGCTCCTT GGAACCACAC TCAGACTCAA TGGACTCTGC CTCAAATCCC ACCAACCTTG     1500

TCAGCACCTC CCAAAGGCAC CGGCCCTTGC TTTCATCCTG TGGCCTCCCA CCAAGCACTG     1560

CCTCAGCTGT GCGCAGGCTA TGCTCCAGGG GGTCGGACCG ATACCTGGAG AGCCGCGATG     1620

CCTCTCGACT GAGTGGCCGG GACCCTCCT CGTGGACAGT CGAGGATGTG ATGCAGTTTG     1680

TCCGGGAAGC TGATCCTCAG CTTGGACCCC ACGCTGACCT GTTTCGCAAA CACGAGATCG     1740

ATGGCAAGGC CCTGCTGCTG CTGCGCAGTG ACATGATGAT GAAGTACATG GGCCTGAAGC     1800

TGGGGCCTGC ACTCAAGCTC TCCTACCACA TTGACCGGCT GAAGCAGGGC AAGTTCTGAA     1860

CCAGGAGAGG CAGCCTAGAC AACCAAGTGG CAGCAGGTGG GGGCATTCTT CTAAGAATGA     1920

GGGGCATCAG CCCACCCCAG GCACCTCAGT GGGGTTCCGG GCCACCTCAG GACTCCAAGA     1980

GGCTGTGTGG AGCCACCACT CCTAGCCACA GCTGCCATGA TAAGTCCTTC CATGAAGGAC     2040

TGAGGAGGGA GAGTGGGGGT CCAGGGCTGG TGCTGCTCTT CCCTCAGCTC TGCCGGGGCT     2100

CTAAGGTCCC TCTATTTATT TCTCAACCCT GGCTGGCCTC TCACCAGGAG TTTAGGCTGA     2160

ATGCCTTCCA CGTGATGGAG GAAAAGGCCA ACTCTGTCCT GGTCTTGCTG TGGCACCCCA     2220

TCGCCCCACA GCTCGTACCT TCTCACCAGA TTCCCCTGAA TCCAAACTCG TGGTGCAAAC     2280

CTCTACCTTT TTTACAAAAA GATCTTATTG TTAATTTATT GTTTCTGGCA CTTGGGCAAA     2340

CCCTGTAGTT AATACTCCTC CCACACTAGA CACTGGGTTT CAGGAGGAGG GAGACTGCCC     2400

TGCTTTGGTC CCAGAGAGGC CCTCTGCAGA TAGGCGTGGC CCCTCTTCAG AGGACACTAC     2460

CCTAGGGCAC TTTCTCTTTG AGGTGGAGAG ACCCATAAAG CCTTGACCAC ATCACTCCAT     2520

ATGGGGAGGA GAAGGATCCC TGTCACCTTC TCCTCTCTTC ACGGGGCCCT TTTGCAGCCC     2580

TAGGCCTCAT CTGTGGGAAG GGAGTCCCTG GCTCATACTG CCCCCACCAC AGCTCCTTGC     2640

CCTGGCCAGA ACTGCTGTCG AAGAAAATCA GGCCGGAAGG CCAAGAAGGC GCTAAGGGGG     2700

ATGGAGGGC AGGTTTTCCA GGCTGGAGTC GGTTCCACCC ACTCGCCTGT CCACAGGCTT     2760

CCTTGTAAGC AAGTCAGCAG CACAGCTACT CACGCTGCCA TCTGGACTTA TTTTATGTCA     2820

ATCTGTTTAT AAATAAAAAC CAATATAGGG AATTC                               2855

(2) INFORMATION FOR SEQ ID NO:2:

(i) SEQUENCE CHARACTERISTICS:
            (A) LENGTH: 620 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:2:
```

```
Ile Pro Asn His Asn Asn Ala Gly His Phe Thr Trp Asp Lys Tyr Leu
 1               5                  10                  15
Lys Glu Thr Cys Ser Val Pro Ala Pro Val His Cys Phe Lys Gln Ser
                20                  25                  30
Tyr Thr Pro Pro Ser Asn Glu Phe Lys Ile Ser Met Lys Leu Glu Ala
            35                  40                  45
Gln Asp Pro Arg Asn Thr Thr Ser Thr Cys Ile Ala Thr Val Val Gly
 50                  55                  60
Leu Thr Gly Ala Arg Leu Arg Leu Arg Leu Asp Gly Ser Asp Asn Lys
 65                  70                  75                  80
Asn Asp Phe Trp Arg Leu Val Asp Ser Ala Glu Ile Gln Pro Ile Gly
                85                  90                  95
Asn Cys Glu Lys Asn Gly Gly Met Leu Gln Pro Leu Gly Phe Arg
                100                 105                 110
Leu Asn Ala Ser Ser Trp Pro Met Phe Leu Leu Lys Thr Leu Asn Gly
            115                 120                 125
Ala Glu Met Ala Pro Ile Arg Ile Phe His Lys Glu Pro Pro Ser Pro
130                 135                 140
Ser His Asn Phe Phe Lys Met Gly Met Lys Leu Glu Ala Val Asp Arg
145                 150                 155                 160
Lys Asn Pro His Phe Ile Cys Pro Ala Thr Ile Gly Glu Val Arg Gly
                165                 170                 175
Ser Glu Val Leu Val Thr Phe Asp Gly Trp Arg Gly Ala Phe Asp Tyr
            180                 185                 190
Trp Cys Arg Phe Asp Ser Arg Asp Ile Phe Pro Val Gly Trp Cys Ser
                195                 200                 205
Leu Thr Gly Asp Asn Leu Gln Pro Pro Gly Thr Lys Val Val Ile Pro
210                 215                 220
Lys Asn Pro Tyr Pro Ala Ser Asp Val Asn Thr Glu Lys Pro Ser Ile
225                 230                 235                 240
His Ser Ser Thr Lys Thr Val Leu Glu His Gln Pro Gly Gln Arg Gly
                245                 250                 255
Arg Lys Pro Gly Lys Lys Arg Gly Arg Thr Pro Lys Thr Leu Ile Ser
                260                 265                 270
His Pro Ile Ser Ala Pro Ser Lys Thr Ala Glu Pro Leu Lys Phe Pro
            275                 280                 285
Lys Lys Arg Gly Pro Lys Pro Gly Ser Lys Arg Lys Pro Arg Thr Leu
290                 295                 300
Leu Asn Pro Pro Pro Ala Ser Pro Thr Thr Ser Thr Pro Glu Pro Asp
305                 310                 315                 320
Thr Ser Thr Val Pro Gln Asp Ala Ala Thr Ile Pro Ser Ser Ala Met
                325                 330                 335
Gln Ala Pro Thr Val Cys Ile Tyr Leu Asn Lys Asn Gly Ser Thr Gly
            340                 345                 350
Pro His Leu Asp Lys Lys Val Gln Gln Leu Pro Asp His Phe Gly
            355                 360                 365
Pro Ala Arg Ala Ser Val Val Leu Gln Gln Ala Val Gln Ala Cys Ile
370                 375                 380
Asp Cys Ala Tyr His Gln Lys Thr Val Phe Ser Phe Leu Lys Gln Gly
385                 390                 395                 400
His Gly Gly Glu Val Ile Ser Ala Val Phe Asp Arg Glu Gln His Thr
                405                 410                 415
Leu Asn Leu Pro Ala Val Asn Ser Ile Thr Tyr Val Leu Arg Phe Leu
```

```
                    420             425             430
Glu Lys Leu Cys His Asn Leu Arg Ser Asp Asn Leu Phe Gly Asn Gln
            435                 440                 445

Pro Phe Thr Gln Thr His Leu Ser Leu Thr Ala Ile Glu Tyr Ser His
    450                 455                 460

Ser His Asp Arg Tyr Leu Pro Gly Glu Thr Phe Val Leu Gly Asn Ser
465                 470                 475                 480

Leu Ala Arg Ser Leu Glu Pro His Ser Asp Ser Met Asp Ser Ala Ser
                485                 490                 495

Asn Pro Thr Asn Leu Val Ser Thr Ser Gln Arg His Arg Pro Leu Leu
                500                 505                 510

Ser Ser Cys Gly Leu Pro Pro Ser Thr Ala Ser Ala Val Arg Arg Leu
            515                 520                 525

Cys Ser Arg Gly Ser Asp Arg Tyr Leu Glu Ser Arg Asp Ala Ser Arg
            530                 535                 540

Leu Ser Gly Arg Asp Pro Ser Ser Trp Thr Val Glu Asp Val Met Gln
545                 550                 555                 560

Phe Val Arg Glu Ala Asp Pro Gln Leu Gly Pro His Ala Asp Leu Phe
                565                 570                 575

Arg Lys His Glu Ile Asp Gly Lys Ala Leu Leu Leu Arg Ser Asp
                580                 585                 590

Met Met Met Lys Tyr Met Gly Leu Lys Leu Gly Pro Ala Leu Lys Leu
            595                 600                 605

Ser Tyr His Ile Asp Arg Leu Lys Gln Gly Lys Phe
610                 615                 620

(2) INFORMATION FOR SEQ ID NO:3:

(i) SEQUENCE CHARACTERISTICS:
        (A) LENGTH: 3327 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

GCGGAAACAT GGCGGCGGGA AGGGAGTGAG CCGCCCCGCG CCCCCGCCGC GCCCTCAGAT        60

GGAGAAATTA GCATACAAAG AAACTGACTT GTCAGAAGTC AGAGCAAGGT ATTGGTGGAT       120

CCAGGGATAA ATCCCAAACT TCTTAACCCC TAGACCGGTT TTTAGTCCAT TGACTATGCA       180

GCCTAATGTG ATAGACTGGA GTGATGTTAG AAAACACAAA TATGGTCACC TATCAGAGTC       240

TGCATCCCAA TATCAAGAAG CTGCTGACAT CCTGGATCTA GGGTTGTAAA GAAGATTACA       300

TGAGCTAATG GATGTGAAAA CATCTTAAAA ACTCTCAAAT ACTTTTCAAC TTTGGAGGAT       360

TATTATGATT TTCATTCTGT TCAGCGGCTA TACTCAGACT TTACTCTAAA AGTCAAATCT       420

TCTGACATTC TTTGAAGTGA AGCATTCTAT GAATGTGAGC TGAAGAAATG AATGAAATGA       480

AATAATGCAG TCATTTTAC CTGGGACAAA TACCTAAAAG AAACATGTTC AGTCCCAGCG        540

CCTGTCCATT GCTTCAAGCA GTCCTACACA CCTCCAAGCA ACGAGTTCAA GATCAGTATG       600

AAATTGGAAG CACAGGACCC CAGGAACACC ACATCCACCT GTATTGCCAC AGTAGTTGGA       660

CTGACAGGTG CCCGCCTTCG CCTGCGCCTT GATGGGAGCG ACAACAAAAA TGACTTCTGG       720

CGGCTGGTTG ACTCAGCTGA AATCCAGCCT ATTGGGAACT GTGAAAAGAA TGGGGGTATG       780

CTACAGCCAC CTCTTGGATT TCGGCTGAAT GCGTCTTCTT GGCCCATGTT CCTTTTGAAG       840

ACGCTAAATG GAGCAGAGAT GGCTCCCATC AGGATTTTCC ACAAGGAGCC ACCATCGCCT       900
```

```
TCCCACAACT TCTTCAAAAT GGGAATGAAG CTAGAAGCTG TGGACAGGAA GAACCCTCAT      960

TTCATTTGCC CAGCCACTAT TGGGGAGGTT CGGGGCTCAG AGGTGCTTGT CACTTTTGAT     1020

GGGTGGCGAG GGGCCTTTGA CTACTGGTGC CGCTTCGACT CCCGAGACAT CTTCCCTGTG     1080

GGCTGGTGTT CCTTGACTGG AGACAACCTG CAGCCTCCTG GCACCAAAGT TGTGATTCCA     1140

AAGAATCCCT ATCCTGCCTC CGATGTGAAT ACTGAGAAGC CCAGCATCCA CAGCAGCACC     1200

AAAACTGTCT TGGAACATCA ACCAGGGCAG AGGGGCGTA AACCAGGAAA GAAGCGGGGC      1260

CGGACACCCA AGACCCTAAT TTCCCATCCC ATCTCTGCCC CATCCAAGAC AGCTGAACCT     1320

TTGAAATTCC CAAAGAAGAG AGGTCCCAAA CCTGGCAGCA AGAGGAAACC TCGGACTTTG     1380

CTGAACCCAC CACCTGCCTC ACCAACAACC AGCACTCCTG AACCGGATAC CAGCACTGTA     1440

CCCCAGGATG CTGCCACCAT CCCCAGCTCA GCCATGCAGG CCCCAACAGT TTGTATCTAC     1500

TTGAACAAGA ATGGCAGCAC AGGCCCCCAC TTAGATAAGA AGAAGGTCCA GCAACTCCCT     1560

GACCATTTTG GACCAGCCCG TGCCTCTGTG GTGTTGCAGC AGGCTGTCCA GGCCTGTATC     1620

GACTGTGCTT ATCACCAGAA AACCGTCTTC AGCTTCCTCA AGCAAGGCCA TGGTGGTGAG     1680

GTTATCTCAG CCGTGTTTGA CCGGGAACAG CATACCCTCA ACCTCCCAGC AGTCAACAGC     1740

ATCACCTACG TCCTCCGCTT CCTGGAGAAA CTCTGCCACA ACCTTCGTAG TGACAATCTG     1800

TTTGGCAACC AGCCCTTTAC ACAGACTCAC TTGTCACTCA CTGCCATAGA GTACAGCCAC     1860

AGCCACGACA GGTACCTACC AGGTGAAACC TTTGTCCTGG GAATAGTCT GGCCCGCTCC      1920

TTGGAACCAC ACTCAGACTC AATGGACTCT GCCTCAAATC CCACCAACCT TGTCAGCACC     1980

TCCCAAAGGC ACCGGCCCTT GCTTTCATCC TGTGGCCTCC CACCAAGCAC TGCCTCAGCT     2040

GTGCGCAGGC TATGCTCCAG GGGGTCGGAC CGATACCTGG AGAGCCGCGA TGCCTCTCGA     2100

CTGAGTGGCC GGGACCCCTC CTCGTGGACA GTCGAGGATG TGATGCAGTT TGTCCGGGAA     2160

GCTGATCCTC AGCTTGGACC CCACGCTGAC CTGTTTCGCA AACACGAGAT CGATGGCAAG     2220

GCCCTGCTGC TGCTGCGCAG TGACATGATG ATGAAGTACA TGGGCCTGAA GCTGGGGCCT     2280

GCACTCAAGC TCTCCTACCA CATTGACCGG CTGAAGCAGG GCAAGTTCTG AACCAGGAGA     2340

GGCAGCCTAG ACAACCAAGT GGCAGCAGGT GGGGGCATTC TTCTAAGAAT GAGGGGCATC     2400

AGCCCACCCC AGGCACCTCA GTGGGGTTCC GGGCCACCTC AGGACTCCAA GAGGCTGTGT     2460

GGAGCCACCA CTCCTAGCCA CAGCTGCCAT GATAAGTCCT TCCATGAAGG ACTGAGGAGG     2520

GAGAGTGGGG GTCCAGGGCT GGTGCTGCTC TTCCCTCAGC TCTGCCGGGG CTCTAAGGTC     2580

CCTCTATTTA TTTCTCAACC CTGGCTGGCC TCTCACCAGG AGTTTAGGCT GAATGCCTTC     2640

CACGTGATGG AGGAAAAGGC CAACTCTGTC CTGGTCTTGC TGTGGCACCC CATCGCCCCA     2700

CAGCTCGTAC CTTCTCACCA GATTCCCCTG AATCCAAACT CGTGGTGCAA ACCTCTACCT     2760

TTTTTACAAA AAGATCTTAT TGTTAATTTA TTGTTTCTGG CACTTGGGCA AACCCTGTAG     2820

TTAATACTCC TCCCACACTA GACACTGGGT TTCAGGAGGA GGGAGACTGC CCTGCTTTGG     2880

TCCCAGAGAG GCCCTCTGCA GATAGGCGTG GCCCCTCTTC AGAGGACACT ACCCTAGGGC     2940

ACTTTCTCTT TGAGGTGGAG AGACCCATAA AGCCTTGACC ACATCACTCC ATATGGGGAG     3000

GAGAAGGATC CCTGTCACCT TCTCCTCTCT TCACGGGGCC CTTTTGCAGC CCTAGGCCTC     3060

ATCTGTGGGA AGGGAGTCCC TGGCTCATAC TGCCCCCACC ACAGCTCCTT GCCCTGGCCA     3120

GAACTGCTGT CGAAGAAAAT CAGGCCGGAA GGCCAAGAAG GCGCTAAGGG GGATGGGAGG     3180

GCAGGTTTTC CAGGCTGGAG TCGGTTCCAC CCACTCGCCT GTCCACAGGC TTCCTTGTAA     3240

GCAAGTCAGC AGCACAGCTA CTCACGCTGC CATCTGGACT TATTTTATGT CAATCTGTTT     3300
```

ATAAATAAAA ACCAATATAG GGAATTC        3327

(2) INFORMATION FOR SEQ ID NO:4:

(i) SEQUENCE CHARACTERISTICS:
        (A) LENGTH: 577 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Met Lys Leu Glu Ala Gln Asp Pro Arg Asn Thr Thr Ser Thr Cys Ile
1               5                   10                  15

Ala Thr Val Val Gly Leu Thr Gly Ala Arg Leu Arg Leu Arg Leu Asp
            20                  25                  30

Gly Ser Asp Asn Lys Asn Asp Phe Trp Arg Leu Val Asp Ser Ala Glu
        35                  40                  45

Ile Gln Pro Ile Gly Asn Cys Glu Lys Asn Gly Gly Met Leu Gln Pro
    50                  55                  60

Pro Leu Gly Phe Arg Leu Asn Ala Ser Ser Trp Pro Met Phe Leu Leu
65                  70                  75                  80

Lys Thr Leu Asn Gly Ala Glu Met Ala Pro Ile Arg Ile Phe His Lys
                85                  90                  95

Glu Pro Pro Ser Pro Ser His Asn Phe Phe Lys Met Gly Met Lys Leu
            100                 105                 110

Glu Ala Val Asp Arg Lys Asn Pro His Phe Ile Cys Pro Ala Thr Ile
        115                 120                 125

Gly Glu Val Arg Gly Ser Glu Val Leu Val Thr Phe Asp Gly Trp Arg
    130                 135                 140

Gly Ala Phe Asp Tyr Trp Cys Arg Phe Asp Ser Arg Asp Ile Phe Pro
145                 150                 155                 160

Val Gly Trp Cys Ser Leu Thr Gly Asp Asn Leu Gln Pro Pro Gly Thr
                165                 170                 175

Lys Val Val Ile Pro Lys Asn Pro Tyr Pro Ala Ser Asp Val Asn Thr
            180                 185                 190

Glu Lys Pro Ser Ile His Ser Ser Thr Lys Thr Val Leu Glu His Gln
        195                 200                 205

Pro Gly Gln Arg Gly Arg Lys Pro Gly Lys Arg Gly Arg Thr Pro
    210                 215                 220

Lys Thr Leu Ile Ser His Pro Ile Ser Ala Pro Ser Lys Thr Ala Glu
225                 230                 235                 240

Pro Leu Lys Phe Pro Lys Arg Gly Pro Lys Pro Gly Ser Lys Arg
                245                 250                 255

Lys Pro Arg Thr Leu Leu Asn Pro Pro Ala Ser Pro Thr Thr Ser
            260                 265                 270

Thr Pro Glu Pro Asp Thr Ser Thr Val Pro Gln Asp Ala Ala Thr Ile
        275                 280                 285

Pro Ser Ser Ala Met Gln Ala Pro Thr Val Cys Ile Tyr Leu Asn Lys
    290                 295                 300

Asn Gly Ser Thr Gly Pro His Leu Asp Lys Lys Val Gln Gln Leu
305                 310                 315                 320

Pro Asp His Phe Gly Pro Ala Arg Ala Ser Val Val Leu Gln Gln Ala
                325                 330                 335

Val Gln Ala Cys Ile Asp Cys Ala Tyr His Gln Lys Thr Val Phe Ser
```

340                 345                 350
Phe Leu Lys Gln Gly His Gly Gly Glu Val Ile Ser Ala Val Phe Asp
                355                 360                 365
Arg Glu Gln His Thr Leu Asn Leu Pro Ala Val Asn Ser Ile Thr Tyr
        370                 375                 380
Val Leu Arg Phe Leu Glu Lys Leu Cys His Asn Leu Arg Ser Asp Asn
385                 390                 395                 400
Leu Phe Gly Asn Gln Pro Phe Thr Gln Thr His Leu Ser Leu Thr Ala
                    405                 410                 415
Ile Glu Tyr Ser His Ser His Asp Arg Tyr Leu Pro Gly Glu Thr Phe
                420                 425                 430
Val Leu Gly Asn Ser Leu Ala Arg Ser Leu Glu Pro His Ser Asp Ser
                435                 440                 445
Met Asp Ser Ala Ser Asn Pro Thr Asn Leu Val Ser Thr Ser Gln Arg
                450                 455                 460
His Arg Pro Leu Leu Ser Ser Cys Gly Leu Pro Pro Ser Thr Ala Ser
465                 470                 475                 480
Ala Val Arg Arg Leu Cys Ser Arg Gly Ser Asp Arg Tyr Leu Glu Ser
                    485                 490                 495
Arg Asp Ala Ser Arg Leu Ser Gly Arg Asp Pro Ser Ser Trp Thr Val
                500                 505                 510
Glu Asp Val Met Gln Phe Val Arg Glu Ala Asp Pro Gln Leu Gly Pro
                515                 520                 525
His Ala Asp Leu Phe Arg Lys His Glu Ile Asp Gly Lys Ala Leu Leu
                530                 535                 540
Leu Leu Arg Ser Asp Met Met Met Lys Tyr Met Gly Leu Lys Leu Gly
545                 550                 555                 560
Pro Ala Leu Lys Leu Ser Tyr His Ile Asp Arg Leu Lys Gln Gly Lys
                    565                 570                 575
Phe (2) INFORMATION FOR SEQ ID NO:5:

(i) SEQUENCE CHARACTERISTICS:
        (A) LENGTH: 3255 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

CGGAAACATG GCGGCGGGAA GGGAGTGAGC CGCCCCGCGC CCCCGCCGCG CCCTCAGATG          60

GAGAAATTAG CATACAAAGA AACTGACTTG TCAGAAGTCA GAGCAAGGTA TTGGTGGATC         120

CAGGGATAAA TCCCAAACTT CTTAACCCCT AGACCGGTTT TTAGTCCATT GACTATGCAG         180

CCTAATGTGA TAGACTGGAG TGATGTTAGA AAACACAAAT ATGGTCACCT ATCAGAGTCT         240

GCATCCCAAT ATCAAGAAGC TGCTGACATC CTGGATCTAG GGTTGTAAAG AAGATTACAT         300

GAGCTAATGG ATGTGAAAAC ATCTTAAAAA CTCTCAAATA CTTTTCAACT TTGGAGGATT         360

ATTATGATTT TCATTCTGTT CAGCGGCCAT ACTCAGACTT TACTCTAAAA GTCAAATCTT         420

CTGACATTCT TTGAAGTGAA GCATTCTATG AATGTGAGCT GAAGAAATGA ATGAAATGAA         480

ATAATGCAGT CCTACACACC TCCAAGCAAC GAGTTCAAGA TCAGTATGAA ATTGGAAGCA         540

CAGGACCCCA GGAACACCAC ATCCACCTGT ATTGCCACAG TAGTTGGACT GACAGGTGCC         600

CGCCTTCGCC TGCGCCTTGA TGGGAGCGAC AACAAAAATG ACTTCTGGCG GCTGGTTGAC         660

```
TCAGCTGAAA TCCAGCCTAT TGGGAACTGT GAAAAGAATG GGGGTATGCT ACAGCCACCT      720

CTTGGATTTC GGCTGAATGC GTCTTCTTGG CCCATGTTCC TTTTGAAGAC GCTAAATGGA      780

GCAGAGATGG CTCCCATCAG GATTTTCCAC AAGGAGCCAC CATCGCCTTC CCACAACTTC      840

TTCAAAATGG GAATGAAGCT AGAAGCTGTG GACAGGAAGA ACCCTCATTT CATTTGCCCA      900

GCCACTATTG GGGAGGTTCG GGGCTCAGAG GTGCTTGTCA CTTTTGATGG GTGGCGAGGG      960

GCCTTTGACT ACTGGTGCCG CTTCGACTCC CGAGACATCT TCCCTGTGGG CTGGTGTTCC     1020

TTGACTGGAG ACAACCTGCA GCCTCCTGGC ACCAAAGTTG TGATTCCAAA GAATCCCTAT     1080

CCTGCCTCCG ATGTGAATAC TGAGAAGCCC AGCATCCACA GCAGCACCAA AACTGTCTTG     1140

GAACATCAAC CAGGGCAGAG GGGGCGTAAA CCAGGAAAGA AGCGGGGCCG GACACCCAAG     1200

ACCCTAATTT CCCATCCCAT CTCTGCCCCA TCCAAGACAG CTGAACCTTT GAAATTCCCA     1260

AAGAAGAGAG GTCCCAAACC TGGCAGCAAG AGGAAACCTC GGACTTTGCT GAACCCACCA     1320

CCTGCCTCAC CAACAACCAG CACTCCTGAA CCGGATACCA GCACTGTACC CCAGGATGCT     1380

GCCACCATCC CCAGCTCAGC CATGCAGGCC CCAACAGTTT GTATCTACTT GAACAAGAAT     1440

GGCAGCACAG GCCCCCACTT AGATAAGAAG AAGGTCCAGC AACTCCCTGA CCATTTTGGA     1500

CCAGCCCGTG CCTCTGTGGT GTTGCAGCAG GCTGTCCAGG CCTGTATCGA CTGTGCTTAT     1560

CACCAGAAAA CCGTCTTCAG CTTCCTCAAG CAAGGCCATG GTGGTGAGGT TATCTCAGCC     1620

GTGTTTGACC GGGAACAGCA TACCCTCAAC CTCCCAGCAG TCAACAGCAT CACCTACGTC     1680

CTCCGCTTCC TGGAGAAACT CTGCCACAAC CTTCGTAGTG ACAATCTGTT TGGCAACCAG     1740

CCCTTTACAC AGACTCACTT GTCACTCACT GCCATAGAGT ACAGCCACAG CCACGACAGG     1800

TACCTACCAG GTGAAACCTT TGTCCTGGGG AATAGTCTGG CCCGCTCCTT GGAACCACAC     1860

TCAGACTCAA TGGACTCTGC CTCAAATCCC ACCAACCTTG TCAGCACCTC CCAAAGGCAC     1920

CGGCCCTTGC TTTCATCCTG TGGCCTCCCA CCAAGCACTG CCTCAGCTGT GCGCAGGCTA     1980

TGCTCCAGGG GGTCGGACCG ATACCTGGAG AGCCGCGATG CCTCTCGACT GAGTGGCCGG     2040

GACCCCTCCT CGTGGACAGT CGAGGATGTG ATGCAGTTTG TCCGGGAAGC TGATCCTCAG     2100

CTTGGACCCC ACGCTGACCT GTTTCGCAAA CACGAGATCG ATGGCAAGGC CCTGCTGCTG     2160

CTGCGCAGTG ACATGATGAT GAAGTACATG GGCCTGAAGC TGGGGCCTGC ACTCAAGCTC     2220

TCCTACCACA TTGACCGGCT GAAGCAGGGC AAGTTCTGAA CCAGGAGAGG CAGCCTAGAC     2280

AACCAAGTGG CAGCAGGTGG GGGCATTCTT CTAAGAATGA GGGGCATCAG CCCACCCCAG     2340

GCACCTCAGT GGGGTTCCGG GCCACCTCAG GACTCCAAGA GGCTGTGTGG AGCCACCACT     2400

CCTAGCCACA GCTGCCATGA TAAGTCCTTC CATGAAGGAC TGAGGAGGGA GAGTGGGGGT     2460

CCAGGGCTGG TGCTGCTCTT CCCTCAGCTC TGCCGGGGCT CTAAGGTCCC TCTATTTATT     2520

TCTCAACCCT GGCTGGCCTC TCACCAGGAG TTTAGGCTGA ATGCCTTCCA CGTGATGGAG     2580

GAAAAGGCCA ACTCTGTCCT GGTCTTGCTG TGGCACCCCA TCGCCCCACA GCTCGTACCT     2640

TCTCACCAGA TTCCCCTGAA TCCAAACTCG TGGTGCAAAC CTCTACCTTT TTTACAAAAA     2700

GATCTTATTG TTAATTTATT GTTTCTGGCA CTTGGGCAAA CCCTGTAGTT AATACTCCTC     2760

CCACACTAGA CACTGGGTTT CAGGAGGAGG GAGACTGCCC TGCTTTGGTC CCAGAGAGGC     2820

CCTCTGCAGA TAGGCGTGGC CCCTCTTCAG AGGACACTAC CCTAGGGCAC TTTCTCTTTG     2880

AGGTGGAGAG ACCCATAAAG CCTTGACCAC ATCACTCCAT ATGGGGAGGA GAAGGATCCC     2940

TGTCACCTTC TCCTCTCTTC ACGGGGCCCT TTTGCAGCCC TAGGCCTCAT CTGTGGGAAG     3000

GGAGTCCCTG GCTCATACTG CCCCCACCAC AGCTCCTTGC CCTGGCCAGA ACTGCTGTCG     3060
```

-continued

```
AAGAAAATCA GGCCGGAAGG CCAAGAAGGC GCTAAGGGGG ATGGGAGGGC AGGTTTTCCA    3120

GGCTGGAGTC GGTTCCACCC ACTCGCCTGT CCACAGGCTT CCTTGTAAGC AAGTCAGCAG    3180

CACAGCTACT CACGCTGCCA TCTGGACTTA TTTTATGTCA ATCTGTTTAT AAATAAAAAC    3240

CAATATAGGG AATTC                                                    3255
```

(2) INFORMATION FOR SEQ ID NO:6:

(i) SEQUENCE CHARACTERISTICS:
        (A) LENGTH: 591 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

```
Met Gln Ser Tyr Thr Pro Pro Ser Asn Glu Phe Lys Ile Ser Met Lys
1               5                   10                  15

Leu Glu Ala Gln Asp Pro Arg Asn Thr Thr Ser Thr Cys Ile Ala Thr
            20                  25                  30

Val Val Gly Leu Thr Gly Ala Arg Leu Arg Leu Arg Leu Asp Gly Ser
        35                  40                  45

Asp Asn Lys Asn Asp Phe Trp Arg Leu Val Asp Ser Ala Glu Ile Gln
    50                  55                  60

Pro Ile Gly Asn Cys Glu Lys Asn Gly Gly Met Leu Gln Pro Pro Leu
65                  70                  75                  80

Gly Phe Arg Leu Asn Ala Ser Ser Trp Pro Met Phe Leu Leu Lys Thr
                85                  90                  95

Leu Asn Gly Ala Glu Met Ala Pro Ile Arg Ile Phe His Lys Glu Pro
            100                 105                 110

Pro Ser Pro Ser His Asn Phe Phe Lys Met Gly Met Lys Leu Glu Ala
        115                 120                 125

Val Asp Arg Lys Asn Pro His Phe Ile Cys Pro Ala Thr Ile Gly Glu
    130                 135                 140

Val Arg Gly Ser Glu Val Leu Val Thr Phe Asp Gly Trp Arg Gly Ala
145                 150                 155                 160

Phe Asp Tyr Trp Cys Arg Phe Asp Ser Arg Asp Ile Phe Pro Val Gly
                165                 170                 175

Trp Cys Ser Leu Thr Gly Asp Asn Leu Gln Pro Pro Gly Thr Lys Val
            180                 185                 190

Val Ile Pro Lys Asn Pro Tyr Pro Ala Ser Asp Val Asn Thr Glu Lys
        195                 200                 205

Pro Ser Ile His Ser Ser Thr Lys Thr Val Leu Glu His Gln Pro Gly
    210                 215                 220

Gln Arg Gly Arg Lys Pro Gly Lys Arg Gly Arg Thr Pro Lys Thr
225                 230                 235                 240

Leu Ile Ser His Pro Ile Ser Ala Pro Ser Lys Thr Ala Glu Pro Leu
                245                 250                 255

Lys Phe Pro Lys Lys Arg Gly Pro Lys Pro Gly Ser Lys Arg Lys Pro
            260                 265                 270

Arg Thr Leu Leu Asn Pro Pro Ala Ser Pro Thr Thr Ser Thr Pro
        275                 280                 285

Glu Pro Asp Thr Ser Thr Val Pro Gln Asp Ala Ala Thr Ile Pro Ser
    290                 295                 300

Ser Ala Met Gln Ala Pro Thr Val Cys Ile Tyr Leu Asn Lys Asn Gly
```

```
            305                 310                 315                 320
    Ser Thr Gly Pro His Leu Asp Lys Lys Val Gln Gln Leu Pro Asp
                    325                 330                 335

His Phe Gly Pro Ala Arg Ala Ser Val Val Leu Gln Gln Ala Val Gln
                    340                 345                 350

Ala Cys Ile Asp Cys Ala Tyr His Gln Lys Thr Val Phe Ser Phe Leu
                    355                 360                 365

Lys Gln Gly His Gly Gly Glu Val Ile Ser Ala Val Phe Asp Arg Glu
                    370                 375                 380

Gln His Thr Leu Asn Leu Pro Ala Val Asn Ser Ile Thr Tyr Val Leu
    385                 390                 395                 400

Arg Phe Leu Glu Lys Leu Cys His Asn Leu Arg Ser Asp Asn Leu Phe
                    405                 410                 415

Gly Asn Gln Pro Phe Thr Gln Thr His Leu Ser Leu Thr Ala Ile Glu
                    420                 425                 430

Tyr Ser His Ser His Asp Arg Tyr Leu Pro Gly Glu Thr Phe Val Leu
                    435                 440                 445

Gly Asn Ser Leu Ala Arg Ser Leu Glu Pro His Ser Asp Ser Met Asp
                    450                 455                 460

Ser Ala Ser Asn Pro Thr Asn Leu Val Ser Thr Ser Gln Arg His Arg
    465                 470                 475                 480

Pro Leu Leu Ser Ser Cys Gly Leu Pro Pro Ser Thr Ala Ser Ala Val
                    485                 490                 495

Arg Arg Leu Cys Ser Arg Gly Ser Asp Arg Tyr Leu Glu Ser Arg Asp
                    500                 505                 510

Ala Ser Arg Leu Ser Gly Arg Asp Pro Ser Ser Trp Thr Val Glu Asp
                    515                 520                 525

Val Met Gln Phe Val Arg Glu Ala Asp Pro Gln Leu Gly Pro His Ala
    530                 535                 540

Asp Leu Phe Arg Lys His Glu Ile Asp Gly Lys Ala Leu Leu Leu Leu
    545                 550                 555                 560

Arg Ser Asp Met Met Met Lys Tyr Met Gly Leu Lys Leu Gly Pro Ala
                    565                 570                 575

Leu Lys Leu Ser Tyr His Ile Asp Arg Leu Lys Gln Gly Lys Phe
                    580                 585                 590

(2) INFORMATION FOR SEQ ID NO:7:

(i) SEQUENCE CHARACTERISTICS:
        (A) LENGTH: 3065 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

CTAGAATTCA GCGGCCGCTT AATTCTAGCT GGATGGGAGT GAGCCGCCCG CGCCCCGCGC      60

CGCTGTCGCC CTCAGATGGA GAGATTAAAT CACAGAGAAA CTAACTTGTC AGAGGTCAGA     120

GCAAGGTGTA GGTGGATCCA GGAATAAGTC TCAAGCTTCA TCACTCCTTG CTTAGTTTTA     180

GGCCATTGAC TATGCAGCCT AGTGACTGGA ATGATGTGAA AAAACCTAAG TATGGTCACT     240

TGTCAGAGTC TGCATCTCAA TATCAAGAAT CTGTTGACAT CCTGGAGCTA GCATCTAGTG     300

CTTTTTTGCAT GGCCCAAAGG GGCCCTGTGC TGCTCCACTA CAGAGGAAAA TTCAAGAAAT     360

GCTGGTTTGC TACAGTGTTT TAGCTTGTGA GAGTCTCTGG GACCTTCCCT GCTCCATCAT     420
```

```
GGGGTCACCT CTAGGTCATT TTACCTGGGA CAAATACCTA AAAGAAACAT GTTCAGTCCC    480

AGCGCCTGTC CATTGCTTCA AGCAGTCCTA CACACCTCCA AGTAATGAGT TCAAGATCAG    540

CATGAAATTG GAAGCACAGG ATCCCAGGAA CACCACATCC ACCTGTATTG CCACGGTCGT    600

TGGATTGACA GGTGCCCGAC TTCGTCTGCG CCTTGATGGC AGTGACAACA AGAATGACTT    660

CTGGAGACTG GTTGACTCCT CTGAAATCCA GCCAATTGGA AACTGTGAGA AGAATGGCGG    720

GATGCTGCAG CCCCCTCTAG GATTTCGGCT GAATGCCTCC TCTTGGCCCA TGTTCCTTTT    780

GAAGACACTA AATGGAGCAG AGATGGCTCC CATCAAGATT TTCCATAAGG AGCCACCATC    840

ACCTTCCCAC AACTTCTTCA AAATGGGAAT GAAGTTAGAA GCTGTAGACA GAAAGAACCC    900

TCATTTCATT TGCCCAGCCA CTATTGGAGA AGTTCGAGGC GCAGAAGTGC TAGTCACCTT    960

TGATGGGTGG CGAGGCGCAT TTGACTACTG GTGCCGCTTT GACTCCCGGG ACATCTTTCC   1020

TGTGGGCTGG TGTTCTTTGA CTGGAGATAA CCTGCAGCCA CCTGGCACCA AAGTTGTGAT   1080

TCCAAAGAAT CCGTCCCCTT CATCTGATGT GAGCACTGAG AAGCCCAGCA TCCACAGCAC   1140

CAAAACTGTC TTGGAGCATC AGCCAGGGCA GAGGGGCCGC AAACCAGGAA AGAAGCGGGG   1200

CCGAACACCC AAGATCCTTA TTCCCCATCC CACCTCTACC CCATCCAAGT CAGCTGAACC   1260

TTTGAAATTT CCAAAGAAGA GAGGTCCCAA GCCTGGCAGT AAGAGGAAAC CTCGGACTTT   1320

GCTGAGCCCA CCACCCACCT CACCAACAAC CAGCACCCCT GAACCGGACA CCAGCACTGT   1380

TCCTCAAGAT GCTGCCACCG TCCCAAGTTC AGCCATGCAG GCCCCCACAG TTTGTATCTA   1440

CTTGAACAAG AGCGGCAGCA CGGGCCCCCA CCTGGATAAA AAGAAGATCC AACAACTCCC   1500

TGACCATTTT GGGCCAGCCC GTGCCTCTGT GGTGCTGCAG CAGGCTGTCC AGGCTTGCAT   1560

TGACTGTGCT TATCACCAGA AAACTGTCTT CAGCTTCCTC AAACAGGGCC ACGGCGGTGA   1620

AGTCATTTCA GCCGTGTTTG ACCGGGAACA GCACACTCTG AACCTCCCAG CAGTCAACAG   1680

CATCACCTAT GTCCTCCGTT TCCTGGAGAA GCTCTGCCAC AACCTTCGAA GTGACAATCT   1740

GTTTGGCAAC CAGCCCTTTA CACAGACTCA CTTATCACTC ACTGCCACAG AGTATAATCA   1800

CAACCACGAC AGGTACCTAC CAGGTGAAAC CTTTGTCCTG GGAATAGCC TGGCCCGGTC    1860

CTTGGAGACA CACTCAGACC TGATGGATTC TGCCTTGAAG CCTGCCAACC TTGTCAGCAC   1920

ATCCCAAAAC CTTCGGACTC CTGGCTATCG GCCCTTGCTT CCCTCCTGTG GCCTCCCATT   1980

AAGCACTGTC TCTGCTGTGC GTAGGCTCTG CTCTAAGGGA GTGTTAAAAG GAAAAAAGGA   2040

AGAAGGGAT GTGGAGTCAT TTTGGAAACT AAATCATTCC CCAGGGTCAG ATCGACATCT    2100

GGAGAGCCGA GATCCCCCTC GCCTGAGTGG CCGGGACCCC TCCTCATGGA CAGTGGAGGA   2160

TGTGATGCAG TTTGTCCGGG AAGCCGATCC TCAGCTTGGA TCCCATGCTG ACCTCTTCCG   2220

AAAACATGAA ATCGATGGCA AGGCCCTGCT CCTGCTGCGC AGTGACATGA TGATGAAGTA   2280

CATGGGCCTG AAGCTGGGGC CGCCCTCAA GCTCTCCTTT CACATTGACC GGCTGAAGCA    2340

GGGCAAGTTC TGAACAGGAG GCACTCTTCT CCCAGGAAGC CGCCCGCCAG CTCCCAGGCA   2400

CCTTAGTAGG GCTCTGGGTG ACCTCAGGAC TCTAGGAGGC TGGAAAGCCA CCACTGCTAC   2460

CCTTCCTGCC CTGATGTGTC CTTCCATGAA GGACTGAGGA GGGAACAGTG GGCCCGGGGC   2520

TGGTGCTGCT CTTCCCCTTA GCCTGCTGTG GCTCCCAGGC CCTTCTATTT ATTTCTCAAG   2580

GCTAGCCAGC CTCTCTCCAC AAGTTTAGAC GAGCACCTTT CAAGAGATGA GGAAGACGCC   2640

AGCCCTAGGA CCTTGAAAGG CCCTGGTACC CAGGCCCCTT GCCACCTCCT GGGCTTGGCA   2700

TAGTGTCCCA AGGCCCCCAG CTCATGCCTT CTCACTGGAT CCCCAGACTC TGAACTTATG   2760

GTGCAGACCT TTTTTAAAGA GATCCTTTCT TATTGCTAAT TTATTGCTTC TGGCGTTTGG   2820
```

```
ACTTAATGCT TCTCTTGCAC CAAACAGTTT TTTGGAAGAG GGAGACCATC CTCTGGTCCA    2880

GAGAGGGCCT CTCCAGAGAA GTGTGGCCTA TTTCAGAAGA CACTGCCCTA GGGCACTTCT    2940

TCTCTGGAAT GGACAAAGTA TTTGGCTCAC TGAGCAAAAG GTGAGGGTCT CTCTTCCTAC    3000

ACTGGGTCCT TTGTAGCCCC AGTCTTCATC TCTGATGGAG TTTCCCCTCA CCCTGCCCTC    3060

GTGCC                                                                3065
```

(2) INFORMATION FOR SEQ ID NO:8:

(i) SEQUENCE CHARACTERISTICS:
        (A) LENGTH: 664 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

```
Met Leu Val Cys Tyr Ser Val Leu Ala Cys Glu Ser Leu Trp Asp Leu
1               5                   10                  15

Pro Cys Ser Ile Met Gly Ser Pro Leu Gly His Phe Thr Trp Asp Lys
            20                  25                  30

Tyr Leu Lys Glu Thr Cys Ser Val Pro Ala Pro Val His Cys Phe Lys
        35                  40                  45

Gln Ser Tyr Thr Pro Pro Ser Asn Glu Phe Lys Ile Ser Met Lys Leu
    50                  55                  60

Glu Ala Gln Asp Pro Arg Asn Thr Thr Ser Thr Cys Ile Ala Thr Val
65                  70                  75                  80

Val Gly Leu Thr Gly Ala Arg Leu Arg Leu Arg Leu Asp Gly Ser Asp
                85                  90                  95

Asn Lys Asn Asp Phe Trp Arg Leu Val Asp Ser Ser Glu Ile Gln Pro
            100                 105                 110

Ile Gly Asn Cys Glu Lys Asn Gly Gly Met Leu Gln Pro Pro Leu Gly
        115                 120                 125

Phe Arg Leu Asn Ala Ser Ser Trp Pro Met Phe Leu Leu Lys Thr Leu
    130                 135                 140

Asn Gly Ala Glu Met Ala Pro Ile Lys Ile Phe His Lys Glu Pro Pro
145                 150                 155                 160

Ser Pro Ser His Asn Phe Phe Lys Met Gly Met Lys Leu Glu Ala Val
                165                 170                 175

Asp Arg Lys Asn Pro His Phe Ile Cys Pro Ala Thr Ile Gly Glu Val
            180                 185                 190

Arg Gly Ala Glu Val Leu Val Thr Phe Asp Gly Trp Arg Gly Ala Phe
        195                 200                 205

Asp Tyr Trp Cys Arg Phe Asp Ser Arg Asp Ile Phe Pro Val Gly Trp
    210                 215                 220

Cys Ser Leu Thr Gly Asp Asn Leu Gln Pro Pro Gly Thr Lys Val Val
225                 230                 235                 240

Ile Pro Lys Asn Pro Ser Pro Ser Asp Val Ser Thr Glu Lys Pro
                245                 250                 255

Ser Ile His Ser Thr Lys Thr Val Leu Glu His Gln Pro Gly Gln Arg
            260                 265                 270

Gly Arg Lys Pro Gly Lys Lys Arg Gly Arg Thr Pro Lys Ile Leu Ile
        275                 280                 285

Pro His Pro Thr Ser Thr Pro Ser Lys Ser Ala Glu Pro Leu Lys Phe
    290                 295                 300
```

-continued

```
Pro Lys Lys Arg Gly Pro Lys Pro Gly Ser Lys Arg Lys Pro Arg Thr
305                 310                 315                 320

Leu Leu Ser Pro Pro Pro Thr Ser Pro Thr Thr Ser Thr Pro Glu Pro
                325                 330                 335

Asp Thr Ser Thr Val Pro Gln Asp Ala Ala Thr Val Pro Ser Ser Ala
                340                 345                 350

Met Gln Ala Pro Thr Val Cys Ile Tyr Leu Asn Lys Ser Gly Ser Thr
            355                 360                 365

Gly Pro His Leu Asp Lys Lys Lys Ile Gln Gln Leu Pro Asp His Phe
            370                 375                 380

Gly Pro Ala Arg Ala Ser Val Val Leu Gln Gln Ala Val Gln Ala Cys
385                 390                 395                 400

Ile Asp Cys Ala Tyr His Gln Lys Thr Val Phe Ser Phe Leu Lys Gln
                405                 410                 415

Gly His Gly Gly Glu Val Ile Ser Ala Val Phe Asp Arg Glu Gln His
                420                 425                 430

Thr Leu Asn Leu Pro Ala Val Asn Ser Ile Thr Tyr Val Leu Arg Phe
            435                 440                 445

Leu Glu Lys Leu Cys His Asn Leu Arg Ser Asp Asn Leu Phe Gly Asn
        450                 455                 460

Gln Pro Phe Thr Gln Thr His Leu Ser Leu Thr Ala Thr Glu Tyr Asn
465                 470                 475                 480

His Asn His Asp Arg Tyr Leu Pro Gly Glu Thr Phe Val Leu Gly Asn
                485                 490                 495

Ser Leu Ala Arg Ser Leu Glu Thr His Ser Asp Leu Met Asp Ser Ala
                500                 505                 510

Leu Lys Pro Ala Asn Leu Val Ser Thr Ser Gln Asn Leu Arg Thr Pro
            515                 520                 525

Gly Tyr Arg Pro Leu Leu Pro Ser Cys Gly Leu Pro Leu Ser Thr Val
            530                 535                 540

Ser Ala Val Arg Arg Leu Cys Ser Lys Gly Val Leu Lys Gly Lys Lys
545                 550                 555                 560

Glu Arg Arg Asp Val Glu Ser Phe Trp Lys Leu Asn His Ser Pro Gly
                565                 570                 575

Ser Asp Arg His Leu Glu Ser Arg Asp Pro Pro Arg Leu Ser Gly Arg
                580                 585                 590

Asp Pro Ser Ser Trp Thr Val Glu Asp Val Met Gln Phe Val Arg Glu
                595                 600                 605

Ala Asp Pro Gln Leu Gly Ser His Ala Asp Leu Phe Arg Lys His Glu
            610                 615                 620

Ile Asp Gly Lys Ala Leu Leu Leu Leu Arg Ser Asp Met Met Met Lys
625                 630                 635                 640

Tyr Met Gly Leu Lys Leu Gly Pro Ala Leu Lys Leu Ser Phe His Ile
                645                 650                 655

Asp Arg Leu Lys Gln Gly Lys Phe
                660
```

MAMMALLIAN SEX COMB ON MIDLEG (MAMMALIAN SCM) ACTS AS A TUMOR SUPPRESSOR

FIELD OF THE INVENTION

The invention relates to a gene, mammalian sex comb on midleg (mammalian Scm), implicated in proliferative disorders, including malignancies, and in developmental processes.

BACKGROUND OF THE INVENTION

Cancer and malignancy therapies have included treatment with chemical toxins, radiation, and surgery. Genes known to be over-expressed or underexpressed in cancer are used for diagnosis of the disease and evaluation of a patient's progression with the disease and treatment.

The study of transcription has provided information about cell differentiation: early in the development of a cell lineage, transcription factors direct development along a particular pathway by activating genes of a differentiated phenotype. Differentiation can involve not only changes in patterns of expressed genes, but also involve the maintenance of those new patterns.

The genetic basis of mammalian development, and the genetic link between development and cancer has not been fully elucidated. There is a need in the art for knowledge of the key genes underlying mammalian cancer, particularly those also implicated in normal mammalian developmental processes.

SUMMARY OF THE INVENTION

In one embodiment of the invention an isolated mammalian Scm (mammalian Scm) polypeptide is provided. The polypeptide comprises a sequence of at least 54 consecutive amino acids of a sequence selected from the group consisting of SEQ ID NO. 2, SEQ ID NO.4, and SEQ ID NO. 6.

In another embodiment of the invention an isolated nucleic acid molecule is provided. The nucleic acid molecule encodes a polypeptide having a sequence selected from the group consisting of SEQ ID NO. 2, SEQ ID NO.4, and SEQ ID NO. 6.

According to yet another embodiment, an isolated nucleic acid molecule is provided which comprises at least 30 contiguous nucleotides selected from the group of sequences consisting of SEQ ID NO: 1, SEQ ID NO:3, AND SEQ ID NO: 5.

In another embodiment of the invention, an antibody preparation is provided. The antibodies specifically bind to an mammalian Scm polypeptide, and do not bind specifically to other mammalian proteins.

In still another embodiment, a method of treating a neoplasm is provided. The method comprises:
contacting a neoplasm with an effective amount of a therapeutic agent comprising a mammalian Scm polypeptide which comprises a sequence selected from the group consisting of SEQ ID NO: 2, SEQ ID NO:4, and SEQ ID NO: 6, whereby growth of the neoplasm is arrested.

In still another embodiment of the invention a method of inducing cell differentiation is provided. The method comprises:
contacting a progenitor cell with a human Scm (hScm) polypeptide which comprises a sequence selected from the group consisting of SEQ ID NO: 2, SEQ ID NO:4, and SEQ ID NO: 6, whereby differentiation of the cell is induced.

According to yet another embodiment of the invention a method of regulating cell growth is provided. The method comprises:
contacting a cell whose growth is uncontrolled with a human Scm (hScm) polypeptide which comprises a sequence selected from the group consisting of SEQ ID NO: 2, SEQ ID NO:4, and SEQ ID NO: 6, whereby growth of the cell is regulated.

According to yet another aspect of the invention a pharmaceutical composition is provided. The composition comprises an effective amount of a therapeutic agent comprising a mammalian Scm polypeptide which comprises a sequence selected from the group consisting of SEQ ID NO: 2, SEQ ID NO:4, and SEQ ID NO: 6, and a pharmaceutically acceptable carrier.

Another aspect of the invention is a method of diagnosing neoplasia. The method comprises:
contacting (a) a tissue sample suspected of neoplasia isolated from a patient with (b) an mammalian Scm gene probe comprising at least 12 nucleotides of a sequence selected from the group consisting of SEQ ID NO: 1, SEQ ID NO: 3, and SEQ ID NO: 5, wherein a tissue which underexpresses mammalian Scm or expresses a variant mammalian Scm is categorized as neoplastic.

According to another embodiment of the invention a method of diagnosing neoplasia is provided. The method comprises:
contacting PCR primers which specifically hybridize with an mammalian Scm gene sequence selected from the group consisting of SEQ ID NO: 1, SEQ ID NO: 3, and SEQ ID NO: 5, with nucleic acids isolated from a tissue suspected of neoplasia;
amplifying mammalian Scm sequences in the nucleic acids of the tissue; and
detecting a mutation in the amplified sequence, wherein a mutation is identified when the amplified sequence differs from a sequence similarly amplified from a normal human tissue.

In yet another embodiment of the invention a method of diagnosing neoplasia is provided. The method comprises:
contacting a bDNA probe with nucleic acids isolated from a tissue suspected of neoplasia, wherein the bDNA probe specifically hybridizes with an mammalian Scm gene sequence selected from the group consisting of SEQ ID NO: 1, SEQ ID NO: 3, and SEQ ID NO: 5;
detecting hybrids formed between the bDNA probe and nucleic acids isolated from the tissue; and
identifying a mutation in the nucleic acids isolated from the tissue by comparing the hybrids formed with hybrids similarly formed using nucleic acids from a normal human tissue.

According to still another aspect of the invention a method of diagnosing neoplasia is provided. The method comprises:
contacting a tissue sample suspected of being neoplastic with an antibody selected from the group consisting of: one which specifically binds to wild-type mammalian Scm as shown in SEQ ID NO:2, 4, or 6, or one which specifically binds to an expressed mammalian Scm variant;
detecting binding of the antibody to components of the tissue sample, wherein a difference in the binding of the antibody to components of the tissue sample, as compared to binding of the antibody to a normal human tissue sample indicates neoplasia of the tissue.

Another aspect of the invention is yet another method of diagnosing neoplasia. The method comprises:

contacting RNA from a tissue suspected of being neoplastic with PCR primers which specifically hybridize to an mammalian Scm gene sequence as shown in SEQ ID NO: 1, 3, or 5, or a bDNA probe which specifically hybridizes to said sequence;

determining quantitative levels of mammalian Scm RNA in the tissue by PCR amplification or bDNA probe detection, wherein lower levels of mammalian Scm RNA as compared to a normal human tissue indicate neoplasia.

Also provided are nucleic acid molecules which can be used in regulating a heterologous coding sequence coordinately with hScm. These sequences include the 5' untranslated region of an hScm gene, the 3' untranslated region of an hScm gene, the promoter region of an hScm gene, and an intron of an hScm gene.

Also provided by the present invention is a method of identifying modulators of hScm function comprising:

contacting a test substance with a human cell which comprises an hScm gene or a reporter construct comprising an hScm promoter and a reporter gene;

quantitating transcription of hScm or the reporter gene in the presence and absence of the test substance, wherein a test substance which increases transcription is a candidate drug for anti-neoplastic therapy.

According to another embodiment a method of diagnosis of neoplasia is provided. The method comprises:

contacting a tissue sample suspected of neoplasia isolated from a patient with an mammalian Scm gene probe comprising at least 12 contiguous nucleotides of a sequence selected from the group consisting of SEQ ID NO: 1, SEQ ID NO: 3, and SEQ ID NO: 5, wherein a tissue which overexpresses mammalian Scm or expresses a variant mammalian Scm is categorized as neoplastic.

In still another aspect of the invention a method of dysregulating cell growth is provided. The method comprises:

contacting a cell whose growth is controlled with a mammalian Scm polypeptide which comprises a sequence selected from the group consisting of SEQ ID NO: 2, SEQ ID NO:4, and SEQ ID NO: 6, whereby growth of the cell is dysregulated.

According to still another aspect of the invention a method of diagnosing neoplasia is provided. The method comprises:

contacting RNA from a tissue suspected of being neoplastic with PCR primers which specifically hybridize to an mammalian Scm gene sequence as shown in SEQ ID NO: 1, 3, or 5, or a bDNA probe which specifically hybridizes to said sequence;

determining quantitative levels of mammalian Scm RNA in the tissue by PCR amplification or bDNA probe detection, wherein higher levels of mammalian Scm RNA as compared to a normal human tissue indicates neoplasia.

Also provided are nucleic acid molecules which can be used in regulating a heterologous coding sequence coordinately with mammalian Scm. These sequences include the 5' untranslated region of an mammalian Scm gene, the 3' untranslated region of an mammalian Scm gene, the promoter region of an mammalian Scm gene, and an intron of an mammalian Scm gene.

Also provided by the present invention is a method of identifying modulators of mammalian Scm function comprising:

contacting a mammalian cell which comprises an mammalian Scm gene or a reporter construct comprising an mammalian Scm promoter and a reporter gene with a test substance;

quantitating transcription of mammalian Scm or the reporter gene in the presence and absence of the test substance, wherein a test substance which decreases transcription is a candidate drug for anti-neoplastic therapy.

DETAILED DESCRIPTION

The inventors have discovered a gene, the mammalian sex comb on midleg (mammalian Scm), that operates to regulate protein expression in mammals, particularly humans. Mammalian Scm may operate by controlling homeotic gene expression. Although the invention is not limited by any theory or mechanism of how the invention works, it is believed that control by this gene involves multiprotein complexes capable of negative regulation of transcription.

The polypeptides of the invention, include the splice variant polypeptides of SEQ ID NO: 2, SEQ ID NO: 4, and SEQ ID NO: 6, which contain different domains of the mammalian Scm gene. The nucleic acid molecules (SEQ ID NO: 1, SEQ ID NO: 3, and SEQ ID NO: 5) encoding the mammalian Scm polypeptides have been cloned from human cells. The polynucleotide of SEQ ID NO: 1 encodes the polypeptide of SEQ ID NO: 2, the polynucleotide of SEQ ID NO: 3 encodes the polypeptide of SEQ ID NO: 4, and the polynucleotide of SEQ ID NO: 5 encodes the polypeptide of SEQ ID NO: 6. Polypeptides comprising at least 6, 10, 20, 30, 40, 50, 54, 60, 65, or 75 amino acids of mammalian Scm are useful as immunogens for raising antibodies and as competitors in immunoassays. They can also be used to purify antibodies. Nucleic acid molecules of at least 15, 20, 30, 40, or 50 contiguous nucleotides are useful as probes for use in diagnostic assays.

Both human and murine Scm, and their coding sequences, are provided herein. There is a striking sequence conservation between murine and human Scm. They are 99% similar at the nucleotide level, and 97% identical at the amino acid level. The proline at position 20 in hScm is substituted with a serine, and the tyrosine at position 59 in hScm is substituted with a phenylalanine. Other mammalian Scm proteins and genes can be obtained by screening of cDNA libraries of a mammalian species with a probe derived from the murine or human sequences. Such techniques are well known in the art, and can be employed by those of skill in the art.

The domains of mammalian Scm protein which appear to be most conserved are those found in the following locations in each of the isoforms of the human proteins. In isoform 1 (amino acid SEQ ID NO:4), the conserved domains are at aa 1 to 80, aa 93 to 128, aa 135 to 142, aa 144 to 166, and aa 527 to 565. In addition the following short segments appear to be well conserved, although they are short: aa 170 to 177, aa 261 to 266, and aa 460 to 467. In isoform 2 (amino acid SEQ ID NO: 6) the conserved domains are: aa 201 to 287, aa 311 to 336, aa 345 to 373, aa 550 to 589, aa 625 to 710, aa 823 to 894, aa 940 to 984, and aa 2170 to 2210. In addition these shorter regions are indicated as conserved: aa 446 to 452, and aa 506 to 511. In isoform 3 (amino acid SEQ ID NO: 2) the domains which appear to be well conserved are: aa 36 to 85, aa 6 to 120, aa 146 to 171, aa 186 to 208, and aa 570 to 608. Regions of conservation are likely functionally important regions which one wants to retain when constructing modifications. In addition, these are most useful in obtaining other species and isoforms of Scm.

The human Scm gene has been mapped to chromosome 1p34. This was accomplished by FISH mapping. Intriguingly, loss of heterozygosity (LOH) for well differentiated gastric cancer and for colon cancer map to this region.

Mammalian Scm is implicated in development, by contributing to the activation or repression of certain genes during development. Thus mammalian Scm can be used therapeutically to change the gene expression pattern and thus the phenotype of a cell. Thus, for example, mammalian Scm can be used to direct differentiation of a progenitor cell. Similarly, inhibition of mammalian Scm will direct a differentiated cell to become less differentiated, i.e., to alter its pattern of gene expression.

Proliferative indications for which an mammalian Scm-based therapeutic agent can be used include, restenosis, benign prostatic hyperplasia, uterine fibroids, retinopathy, psoriasis, keloids, arthritis, wound healing, and premalignant lesions including for example, intestinal polyps, cervical dysplasia, and myeloid dysplasia. Neoplasias that may be treatable with an mammalian Scm-based therapeutic agent, include, but are not limited to, lung carcinoma, colorectal adenocarcinoma, leukemia, Burkitt's lymphoma and melanoma.

The coding region of mammalian Scm can be used for expression of mammalian Scm and for development of mammalian Scm variants for therapeutic applications. Mammalian Scm coding sequence can be used as a probe for diagnosis of disease or biological disorder where overexpression of mammalian Scm occurs, such as, for example, in cancers such as lung carcinoma, colorectal adenocarcinoma, lymphatic cancer, promyelocytic leukemia, Burkitt's lymphoma, and myeloma. The 5' untranslated and 3' untranslated regions of mammalian Scm can also be used diagnostically to the same effect as the mammalian Scm coding sequence, for example, the 5' untranslated region can be isolated and used to probe tissue, for example, lung tissue, where lung carcinoma is suspected. Because mammalian Scm has been shown to be upregulated in lung carcinoma, probing with any portion of the mammalian Scm gene can identify the upregulation of mammalian Scm in the tissue, as an aid to making a diagnosis. Such diagnostic probes may also be used for continued monitoring of a diagnosed patient, for signs of improvement after and during treatment, and for indications of progression of the disease.

Mammalian Scm genes can be cloned and isolated by probing genomic DNA with the coding region of mammalian Scm, or by probing genomic DNA with any probe-length piece (at least 12 nucleotides) of mammalian Scm DNA. A P1 clone of genomic DNA containing hScm (Human Genome Sciences #11267, CMCC #4737) has been deposited at the American Type Culture Collection, Rockville, Md. The genomic DNA can be subcloned into a cloning vector, for example a cosmid vector, for sequencing and assembly of the entire gene sequence. The promoter region of mammalian Scm is useful for expression of mammalian Scm in a gene therapy protocol, and for further analysis of mammalian Scm gene function and regulatory control. Knowledge of promoter region sequences specific for binding transcriptional activators that activate the mammalian Scm promoter can facilitate improved expression of mammalian Scm for therapeutic purposes. The mammalian Scm promoter region may be useful for tissue specific expression of heterologous genes, such as, for treatment of lung carcinoma or colorectal adenocarcinoma. The region immediately 5' of the coding region of mammalian Scm can be used, for example, as a diagnostic probe for cancer or a developmental disorder associated with aberrant mammalian Scm activity. The full length gene, or such non-coding regions of it as the promoter and the 5' or 3' untranslated regions can be isolated by probing genomic DNA with a probe comprising at least about 12 nucleotides of mammalian Scm cDNA, and retrieving a genomic sequence that hybridizes to one of these sequences. The 5' untranslated end and the promoter regions, for example, can be cloned by PCR cloning with random oligonucleotide and a 5' portion of the known coding sequence.

The polypeptides of the invention can further be used to generate monoclonal or polyclonal antibodies. Monoclonal antibodies, are prepared using the method of Kohler and Milstein, as described in Nature (1975) 256: 495–96, or a modification thereof. Antibodies to mammalian Scm, either polyclonal or monoclonal, can be used therapeutically. They are desirably compatible with the host to be treated. For example, for treatment of humans, the antibodies can be human monoclonal antibodies or humanized antibodies, as the term is generally known in the art. Alternatively, single chain antibodies may be used for therapy. Antibodies may act to antagonize or inhibit the polypeptide activity of mammalian Scm, and are also useful in diagnosing a condition characterized by mammalian Scm expression or overexpression, such as, for example, a malignancy condition. Similarly, underexpression can be detected using such antibodies bind specifically to mammalian Scm but not to other human proteins. More preferred is the situation where the antibodies are human species mammalian Scm-specific.

Expression of mammalian Scm can be accomplished by any expression system appropriate for the purpose and conditions presented. Some exemplary expression systems are listed below. Where mammalian Scm itself is used as a therapeutic, the polypeptide can be expressed and subsequently administered to a patient. Alternatively a gene encoding at least a functional portion of mammalian Scm can be administered to a patient for expression in the patient.

Recombinant mammalian Scm may be used as a reagent for diagnostic methods for diagnosis of cancer or a developmental disorder. It may also be used as a therapeutic for inducing differentiation in a population of progenitor cells. Recombinant mammalian Scm can also be used to develop modulators of mammalian Scm for achieving a desired therapeutic effect. Construction and expression of any of the recombinant molecules of the invention can be accomplished by any expression system most appropriate for the task, including, for example, an expression system described below.

Expression Systems

Although the methodology described below is believed to contain sufficient details to enable one skilled in the art to practice the present invention, other constructs can be constructed and purified using standard recombinant DNA techniques as described in, for example, Sambrook et al. (1989), MOLECULAR CLONING: A LABORATORY MANUAL, 2nd ed. (Cold Spring Harbor Press, Cold Spring Harbor, New York); and under current regulations described in United States Dept. of Health and Human Services, National Institutes of Health (NIH) Guidelines for Recombinant DNA Research. The polypeptides of the invention can be expressed in any expression system, including, for example, bacterial, yeast, insect, amphibian and mammalian systems. Expression systems in bacteria include those described in Chang et al., Nature (1978) 275: 615, Goeddel et al., Nature (1979) 281: 544, Goeddel et al., Nucleic Acids Res. (1980) 8: 4057, EP 36,776, U.S. Pat. No. 4,551,433, deBoer et al., Proc. Natl. Acad. Sci. USA (1983) 80: 21–25, and Siebenlist et al., Cell (1980) 20: 269. Expression systems in yeast include those described in Hinnen et al., *Proc. Natl. Acad. Sci. USA* (1978) 75: 1929; Ito et al., *J. Bacteriol.* (1983) 153: 163; Kurtz et al., *Mol. Cell. Biol.* (1986) 6: 142; Kunze et al., *J. Basic Microbiol.* (1985) 25: 141; Gleeson et al., *J. Gen. Microbiol.* (1986) 132: 3459, Roggenkamp et al., *Mol. Gen. Genet.* (1986) 202: 302) Das et al., *J. Bacteriol.* (1984) 158: 1165; De Louvencourt et al., *J. Bacteriol.* (1983) 154: 737, Van den Berg et al., *Bio/Technology* (1990) 8: 135; Kunze et al., *J. Basic Microbiol.* (1985) 25: 141; Cregg et al., *Mol. Cell. Biol.* (1985) 5: 3376, U.S. Pat. No. 4,837,148, U.S. Pat. No. 4,929,555; Beach and Nurse, *Nature* (1981) 300: 706; Davidow et al., *Curr. Genet.* (1985) 10: 380, Gaillardin et al., *Curr. Genet.* (1985) 10: 49, Ballance et al., *Biochem. Biophys. Res. Commun.* (1983) 112: 284–289; Tilburn et al., *Gene* (1983) 26: 205–221, Yelton et al., *Proc. Natl. Acad. Sci. USA* (1984)81: 1470–1474, Kelly and Hynes, *EMBO J.* (1985) 4: 475479; EP 244,234, and WO 91/00357. Expression of heterologous genes in insects can be accomplished as described in U.S. Pat. No. 4,745,051, Friesen et al. (1986) "The Regulation of Baculovirus Gene Expression" in: THE MOLECULAR BIOLOGY OF BACULOVIRUSES (W. Doerfler, ed.), EP 127,839, EP 155,476, and Vlak et al., *J. Gen. Virol.* (1988) 69: 765–776, Miller et al., *Ann. Rev. Microbiol.* (1988) 42: 177, Carbonell et al., *Gene* (1988) 73: 409, Maeda et al., *Nature* (1985) 315: 592–594, Lebacq-Verheyden et al., *Mol. Cel. Biol.* (1988) 8: 3129; Smith et al., *Proc. Natl. Acad. Sci. USA* (1985) 82: 8404, Miyajima et al., *Gene* (1987) 58: 273; and Martin et al., *DNA* (1988) 7.99. Numerous baculoviral strains and variants and corresponding permissive insect host cells from hosts are described in Luckow et al., *Bio/Technology* (1988) 6: 47–55, Miller et al., in GENERIC ENGINEERING (Setlow, J. K. et al. eds.), Vol. 8 (Plenum Publishing, 1986), pp. 277–279, and Maeda et al., *Nature*, (1985) 315: 592–594. Mammalian expression can be accomplished as described in Dijkema et al., *EMBO J.* (1985) 4: 761, Gorman et al., *Proc. Natl. Acad. Sci. USA* (1982b) 79: 6777, Boshart et al., *Cell* (1985) 41: 521 and U.S. Pat. No. 4,399,216. Other features of mammalian expression can be facilitated as described in Ham and Wallace, *Meth. Enz.* (1979) 58: 44, Barnes and Sato, *Anal. Biochem.* (1980) 102: 255, U.S. Pat. No. 4,767,704, U.S. Pat. No. 4,657,866, U.S. Pat. No. 4,927,762, U.S. Pat. No. 4,560,655, WO 90/103430, WO 87/00195, and U.S. Pat. No. RE 30,985.

Constructs including an mammalian Scm coding sequence or constructs including coding sequences for modulators of mammalian Scm can be administered by a gene therapy protocol, either locally or systemically. These constructs can utilize viral or non-viral vectors and can be delivered in vivo or ex vivo or in vitro. Expression of such coding sequence can be driven by endogenous mammalian or heterologous promoters. Expression of the coding sequence in vivo can be either constitutive or regulated.

Gene delivery vehicles (GDVs) are available for delivery of polynucleotides to cells, tissue, or a mammal for expression. For example, a polynucleotide sequence of the invention can be administered either locally or systemically in a GDV. These constructs can utilize viral or non-viral vector approaches in in vivo or ex vivo modality. Expression of such coding sequence can be induced using endogenous mammalian or heterologous promoters. Expression of the coding sequence in vivo can be either constitutive or regulated. The invention includes gene delivery vehicles capable of expressing the contemplated polynucleotides. The gene delivery vehicle is preferably a viral vector and, more preferably, a retroviral, adenoviral, adeno-associated viral (AAV), herpes viral, or alphavirus vectors. The viral vector can also be an astrovirus, coronavirus, orthomyxovirus, papovavirus, paramyxovirus, parvovirus, picornavirus, poxvirus, togavirus viral vector. See generally, Jolly, Cancer Gene Therapy 1:51–64 (1994); Kimura, Human Gene Therapy 5:845–852 (1994), Connelly, Human Gene Therapy 6:185–193 (1995), and Kaplitt, Nature Genetics 6:148–153 (1994). Retroviral vectors are well known in the art and we contemplate that any retroviral gene therapy vector is employable in the invention, including B, C and D type retroviruses, xenotropic retroviruses (for example, NZB-X1, NZB-X2 and NZB9-1 (see O'Neill, J. Vir. 53:160, 1985) polytropic retroviruses (for example, MCF and MCF-MLV (see Kelly, J. Vir. 45:291, 1983), spumaviruses and lentiviruses. See RNA Tumor Viruses, Second Edition, Cold Spring Harbor Laboratory, 1985.

Portions of the retroviral gene therapy vector may be derived from different retroviruses. For example, retroviral LTRs may be derived from a Murine Sarcoma Virus, a tRNA binding site from a Rous Sarcoma Virus, a packaging signal from a Murine Leukemia Virus, and an origin of second strand synthesis from an Avian Leukosis Virus. These recombinant retroviral vectors may be used to generate transduction competent retroviral vector particles by introducing them into appropriate packaging cell lines (see U.S. Ser. No. 07/800,921, filed Nov. 29, 1991). Retrovirus vectors can be constructed for site-specific integration into host cell DNA by incorporation of a chimeric integrase enzyme into the retroviral particle. See, U.S. Ser. No. 08/445,466 filed May 22, 1995. It is preferable that the recombinant viral vector is a replication defective recombinant virus. Packaging cell lines suitable for use with the above-described retrovirus vectors are well known in the art, are readily prepared (see U.S. Ser. No. 08/240,030, filed May 9, 1994; see also WO 92/05266), and can be used to create producer cell lines (also termed vector cell lines or "VCLs") for the production of recombinant vector particles. Preferably, the packaging cell lines are made from human parent cells (e.g., HT1080 cells) or mink parent cell lines, which eliminates inactivation in human serum. Preferred retroviruses for the construction of retroviral gene therapy vectors include Avian Leukosis Virus, Bovine Leukemia, Virus, Murine Leukemia Virus, Mink-Cell Focus-Inducing Virus, Murine Sarcoma Virus, Reticuloendotheliosis Virus and Rous Sarcoma Virus. Particularly preferred Murine Leukemia Viruses include 4070A and 1504A (Hartley and Rowe, J. Virol. 19:19–25, 1976), Abelson (ATCC No. VR-999), Friend (ATCC No. VR-245), Graffi, Gross (ATCC No. VR-590), Kirsten, Harvey Sarcoma Virus and Rauscher (ATCC No. VR-998) and Moloney Murine Leukemia Virus (ATCC No. VR-190). Such retroviruses may be obtained from depositories or collections such as the American Type Culture Collection ("ATCC") in Rockville, Md. or isolated from known sources using commonly available techniques. Exemplary known retroviral gene therapy vectors employable in this invention include those described in GB 2200651; EP No. 415,731; EP No. 345,242; PCT Publication Nos. WO 89/02468, WO 89/05349, WO 89/09271, WO 90/02806, WO 90/07936, WO 90/07936, WO 94/03622, WO 93/25698, WO 93/25234, WO 93/11230, WO 93/10218, and WO 91/02805, in U.S. Pat. Nos. 5,219,740, 4,405,712, 4,861,719, 4,980, 289 and 4,777,127, in U.S. Ser. No. 07/800,921 and in Vile, Cancer Res. 53:3860–3864 (1993); Vile, Cancer Res 53:962–967 (1993); Ram, Cancer Res 53:83–88 (1993); Takamiya, J. Neurosci. Res. 33:493–503 (1992); Baba, J Neurosurg 79:729–735 (1993); Mann, Cell 33:153 (1983); Cane, Proc Natl Acad Sci 81:6349 (1984) and Miller, Human Gene Therapy 1 (1990). Human adenoviral gene therapy vectors are also known in the art and employable in this invention. See, for example, Berkner, Biotechniques 6:616 (1988), and Rosenfeld, Science 252:431 (1991), and PCT Patent Publication Nos. WO 93/07283, WO 93/06223, and WO 93/07282. Exemplary known adenoviral gene therapy vectors employable in this invention include those described in the above-referenced documents and in PCT Patent Publication Nos. WO 94/12649, WO 93/03769, WO 93/19191, WO 94/28938, WO 95/11984, WO 95/00655, WO 95/27071, WO 95/29993, WO 95/34671, WO 96/05320, WO 94/08026, WO 94/11506, WO 93/06223, WO 94/24299, WO 95/14102, WO 95/24297, WO 95/02697, WO 94/28152, WO 94/24299, WO 95/09241, WO 95/25807, WO 95/05835, WO 94/18922 and WO 95/09654. Alternatively, administration of DNA linked to killed adenovirus as described in Curiel, Hum. Gene Ther. 3:147–154 (1992) may be employed. The gene delivery vehicles of the invention also include adenovirus associated virus (AAV) vectors. Leading and preferred examples of such vectors for use in this invention are the AAV-2 basal vectors disclosed in Srivastava, PCT Patent Publication No. WO 93/09239. Most preferred AAV vectors comprise the two AAV inverted terminal repeats in which the native D-sequences are modified by substitution of nucleotides, such that at least 5 native nucleotides and up to 18 native nucleotides, preferably at least 10 native nucleotides up to 18 native nucleotides, most preferably 10 native nucleotides are retained and the remaining nucleotides of the D-sequence are deleted or replaced with non-native nucleotides. The native D-sequences of the AAV inverted terminal repeats are sequences of 20 consecutive nucleotides in each AAV inverted terminal repeat (i.e., there is one sequence at each end) which are not involved in HP formation. The non-native replacement nucleotide may be any nucleotide other than the nucleotide found in the native D-sequence in the same position. Other employable exemplary AAV vectors are pWP-19, pWN-1, both of which are disclosed in Nahreini, Gene 124:257–262 (1993). Another example of such an AAV vector is psub201. See Samulski, J. Virol. 61:3096 (1987). Another exemplary AAV vector is the Double-D ITR vector. How to make the Double D ITR vector is disclosed in U.S. Pat. No. 5,478,745. Still other vectors are those disclosed in Carter, U.S. Pat. No. 4,797,368 and Muzyczka, U.S. Pat. No. 5,139,941, Chartejee, U.S. Pat. No. 5,474,935, and Kotin, PCT Patent Publication No. WO 94/288157. Yet a further example of an AAV vector employable in this invention is SSV9AFABTKneo, which contains the AFP enhance and albumin promoter and directs expression predominantly in the liver. Its structure and how to make it are disclosed in Su,Human Gene Therapy 7:463–470 (1996). Additional AAV gene therapy vectors are described in U.S. Pat. Nos. 5,354,678; 5,173,414; 5,139,941; and 5,252,479. The gene therapy vectors of the invention also include herpes vectors. Leading and preferred examples are herpes simplex virus vectors containing a sequence encoding a thymidine kinase polypeptide such as those disclosed in U.S. Pat. No. 5,288,641 and EP No. 176,170 (Roizman). Additional exemplary herpes simplex virus vectors include HFEM/ICP6-LacZ disclosed in PCT Patent No. WO 95/04139 (Wistar Institute), pHSVlac described in Geller, Science 241:1667–1669 (1988) and in PCT Patent Publication Nos. WO 90/09441 and WO 92/07945, HSV Us3::pgC-lacZ described in Fink, Human Gene Therapy 3:11–19 (1992) and HSV 7134, 2 RH 105 and GALA described in EP No. 453,242 (Breakefield), and those deposited with the ATCC as accession numbers ATCC VR-977 and ATCC VR-260. Alpha virus gene therapy vectors may be employed in this invention. Preferred alpha virus vectors are Sindbis viruses vectors. Togaviruses, Semliki Forest virus (ATCC VR-67; ATCC VR-1247), Middleberg virus (ATCC VR-370), Ross River virus (ATCC VR-373; ATCC VR-1246), Venezuelan equine encephalitis virus (ATCC VR923; ATCC VR-1250; ATCC VR-1249; ATCC VR-532), and those described U.S. Pat. Nos. 5,091,309 and 5,217,879, and PCT Patent Publication No. WO 92/10578. More particularly, those alpha virus vectors described in U.S. Ser. No. 08/405,627, filed Mar. 15, 1995, and U.S. Ser. No. 08/198,450 and in PCT Patent Publication Nos. WO 94/21792, WO 92/10578, and WO 95/07994, and U.S. Pat. Nos. 5,091,309 and 5,217,879 are employable. Such alpha viruses may be obtained from depositories or collections such as the ATCC in Rockville, Md. or isolated from known sources using commonly available techniques. Preferably, alphavirus vectors with reduced cytotoxicity are used (see co-owned U.S. Ser. No. 08/679640). DNA vector systems such as eukaryotic layered expression systems are also useful for expressing the nucleic acids of the invention. See PCT Patent Publication No. WO 95/07994 for a detailed description of eukaryotic layered expression systems. Preferably, the eukaryotic layered expression systems of the invention are derived from alphavirus vectors and most preferably from Sindbis viral vectors. Other viral vectors suitable for use in the present invention include those derived from poliovirus, for example ATCC VR-58 and those described in Evans, Nature 339:385 (1989), and Sabin, J. Biol. Standardization 1:115 (1973); rhinovirus, for example ATCC VR-1110 and those described in Arnold, J Cell Biochem (1990) L401; pox viruses such as canary pox virus or vaccinia virus, for example ATCC VR-111 and ATCC VR-2010 and those described in Fisher-Hoch, Proc Natl Acad Sci 86 (1989) 317, Flexner, Ann NY Acad Sci 569:86 (1989), Flexner, Vaccine 8:17 (1990); in U.S. Pat. Nos. 4,603,112 and 4,769,330 and in WO 89/01973; SV40 virus, for example ATCC VR-305 and those described in Mulligan, Nature 277:108 (1979) and Madzak, J Gen Vir 73:1533 (1992); influenza virus, for example ATCC VR-797 and recombinant influenza viruses made employing reverse genetics techniques as described in U.S. Pat. No. 5,166,057 and in Enami, Proc. Natl. Acad. Sci. 87:3802–3805 (1990); Enami and Palese, J. Virol. 65:2711–2713 (1991); and Luytes, Cell 59:110 (1989), (see also McMicheal., New England J. Med. 309:13 (1983), and Yap, Nature 273:238 (1978) and Nature 277:108, 1979); human immunodeficiency virus as described in EP No. 386,882 and in Buchschacher, J. Vir. 66:2731 (1992); measles virus, for example, ATCC VR-67 and VR-1247 and those described in EP No. 440,219; Aura virus, for example, ATCC VR-368; Bebaru virus, for example, ATCC VR-600 and ATCC VR-1240; Cabassou virus, for example, ATCC VR-922; Chikungunya virus, for example, ATCC VR-64 and ATCC VR-1241; Fort Morgan Virus, for example, ATCC VR-924; Getah virus, for example, ATCC VR-369 and ATCC VR-1243; Kyzylagach virus, for example, ATCC VR-927; Mayaro virus, for example, ATCC VR-66; Mucambo virus, for example, ATCC VR-580 and ATCC VR-1244; Ndumu virus, for example, ATCC VR-371; Pixuna virus, for example, ATCC VR-372 and ATCC VR-1245; Tonate virus, for example, ATCC VR-925; Triniti virus, for example ATCC VR-469; Una virus, for example, ATCC VR-374; Whataroa virus, for example ATCC VR-926; Y-62-33 virus, for example, ATCC VR-375; O'Nyong virus, Eastern encephalitis virus, for example, ATCC VR-65 and ATCC VR-1242; Western encephalitis virus, for example, ATCC VR-70, ATCC VR-1251, ATCC VR-622 and ATCC VR-1252; and coronavirus, for example, ATCC VR-740 and those described in Hamre, Proc. Soc. Exp. Biol. Med. 121:190 (1966). Delivery of the compositions of this invention into cells is not limited to the above mentioned viral vectors. Other delivery methods and media may be employed such as, for example, nucleic acid expression vectors, polycationic condensed DNA linked or unlinked to killed adenovirus alone, for example see U.S. Ser. No. 08/366,787, filed Dec. 30, 1994, and Curiel, Hum Gene Ther 3:147–154 (1992) ligand linked DNA, for example, see Wu, J. Biol. Chem. 264:16985–16987 (1989), eukaryotic cell delivery vehicles cells, for example see U.S. Ser. No. 08/240,030, filed May 9, 1994, and U.S. Ser. No. 08/404,796, deposition of photopolymerized hydrogel materials, hand-held gene transfer particle gun, as described in U.S. Pat. No. 5,149,655, ionizing radiation as described in U.S. Pat. No. 5,206,152 and in PCT Patent Publication No. WO 92/11033, nucleic charge neutralization or fusion with cell membranes. Additional approaches are described in Philip, Mol. Cell. Biol. 14:2411–2418 (1994) and in Woffendin, Proc. Natl. Acad. Sci. 91:1581–585 (1994). Particle mediated gene transfer may be employed, for example see U.S. provisional application No. 60/023,867. Briefly, the sequence can be inserted into conventional vectors that contain conventional control sequences for high level expression, and then be incubated with synthetic gene transfer molecules such as polymeric DNA-binding cations like polylysine, protamine, and albumin, linked to cell targeting ligands such as asialoorosomucoid, as described in Wu and Wu, J. Biol. Chem. 262:4429–4432 (1987), insulin as described in Hucked, Biochem. Pharmacol. 40:253–263 (1990), galactose as described in Plank, Bioconjugate Chem 3:533–539 (1992), lactose or transferrin. Naked DNA may also be employed. Exemplary naked DNA introduction methods are described in PCT Patent Publication No. WO 90/11092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm. Liposomes that can act as gene delivery vehicles are described in U.S. Pat. No. 5,422,120, PCT Patent Publication Nos. WO 95/13796, WO 94/23697, and WO 91/144445, and EP No. 524,968. As described in co-owned U.S. provisional application No. 60/023,867, on non-viral delivery, the nucleic acid sequences can be inserted into conventional vectors that contain conventional control sequences for high level expression, and then be incubated with synthetic gene transfer molecules such as polymeric DNA-binding cations like polylysine, protamine, and albumin, linked to cell targeting ligands such as asialoorosomucoid, insulin, galactose, lactose, or transferrin. Other delivery systems include the use of liposomes to encapsulate DNA comprising the gene under the control of a variety of tissue-specific or ubiquitously-active promoters. Further non-viral delivery suitable for use includes mechanical delivery systems such as the approach described in Woffendin et al., Proc. Natl. Acad. Sci. USA 91(24):11581–11585 (1994). Moreover, the coding sequence and the product of expression of such can be delivered through deposition of photopolymerized hydrogel materials. Other conventional methods for gene delivery that can be used for delivery of the coding sequence include, for example, use of hand-held gene transfer particle gun, as described in U.S. Pat. No. 5,149,655; use of ionizing radiation for activating transferred gene, as described in U.S. Pat. No. 5,206,152 and PCT Patent Publication No. WO 92/11033. Exemplary liposome and polycationic gene delivery vehicles are those described in U.S. Pat. Nos. 5,422,120 and 4,762,915, in PCT Patent Publication Nos. WO 95/13796, WO 94/23697, and WO 91/14445, in EP No. 524,968 and in Stryer, Biochemistry, pages 236–240 (1975) W. H. Freeman, San Francisco, Szoka, Biochem. Biophys. Acta. 600:1 (1980); Bayer, Biochem. Biophys. Acta. 550:464 (1979); Rivnay, Meth. Enzymol. 149:119 (1987); Wang, Proc. Natl. Acad. Sci. 84:7851 (1987); and Plant, Anal. Biochem. 176:420 (1989).

Test compounds can be tested as candidate modulators by testing the ability to increase or decrease the expression of mammalian Scm. The candidate modulators can be derived from any of the various possible sources of candidates, such as for example, libraries of peptides, peptoids, small molecules, polypeptides, antibodies, polynucleotides, small molecules, antisense molecules, ribozymes, cRNA, cDNA, polypeptides presented by phage display. Described below are some exemplary and possible sources of candidates, including synthesized libraries of peptides, peptoids, and small molecules. The exemplary expression systems can be used to generate cRNA or cDNA libraries that can also be screened for the ability to modulate mammalian Scm activity or expression. Candidate molecules screened for the ability to agonize mammalian Scm expression or activity may be useful for inducing differentiation in a population of progenitor cells. Small molecules can be screened for the ability to either affect mammalian Scm expression or affect mammalian Scm function by enhancing or interfering in mammalian Scm's ability to interact with other molecules that mammalian Scm normally interacts with in mammalian Scm's normal function.

Mammalian Scm peptide modulators are screened using any available method. The assay conditions ideally should resemble the conditions under which the mammalian Scm modulation is exhibited in vivo, that is, under physiologic pH, temperature, ionic strength, etc. Suitable antagonists will exhibit strong inhibition of mammalian Scm expression or activity at concentrations that do not cause toxic side effects in the subject. A further alternative agent that can be used herein as a modulator of mammalian Scm is a small molecule antagonist. Small molecules can be designed and screened from a pool of synthetic candidates for ability to modulate mammalian Scm. There exist a wide variety of small molecules, including peptide analogs and derivatives, that can act as inhibitors of proteins and polypeptides. Libraries of these molecules can be screened for those compounds that inhibit the activity or expression of mammalian Scm. Similarly, ribozymes can be screened in assays appropriate for ribozymes, taking into account the special biological or biochemical nature of ribozymes. Assays for affecting mammalian Scm expression can measure mammalian Scm message or protein directly, or can measure a reporter gene expression which is under the control of an mammalian Scm promoter and/or 5' untranslated region (UTR).

Mammalian Scm or a modulator of mammalian Scm can be administered to a patient exhibiting a condition characterized by abnormal cell proliferation, in which aberrant mammalian Scm gene expression is implicated, particularly excessive mammalian Scm activity, or excessive activity controlled or induced by mammalian Scm activity. The modulator can be incorporated into a pharmaceutical composition that includes a pharmaceutically acceptable carrier for the modulator. Suitable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art. Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in REMINGTON'S PHARMACEUTICAL SCIENCES (Mack Pub. Co., N.J. 1991). Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared.

Liposomes are included within the definition of a pharmaceutically acceptable carrier. The term "liposomes" refers to, for example, the liposome compositions described in U.S. Pat. No: 5,422,120, WO 95/13796, WO 94/23697, WO 91/14445 and EP 524,968 B1. Liposomes may be pharmaceutical carriers for the peptides, polypeptides or polynucleotides of the invention, or for combination of these therapeutics.

Any therapeutic of the invention, including, for example, polynucleotides for expression in the patient, or ribozymes or antisense oligonucleotide, can be formulated into an enteric coated tablet or gel capsule according to known methods in the art. These are described in the following patents: U.S. Pat. No. 4,853,230, EP 225,189, AU 9,224, 296, AU 9,230,801, and WO 92144,52. Such a capsule is administered orally to be targeted to the jejunum. At 1 to 4 days following oral administration expression of the polypeptide, or inhibition of expression by, for example a ribozyme or an antisense oligonucleotide, is measured in the plasma and blood, for example by antibodies to the expressed or non-expressed proteins.

Administration of a therapeutic agent of the invention, including for example an mammalian Scm modulator, includes administering a therapeutically effective dose of the therapeutic agent by a means considered or empirically deduced to be effective for inducing the desired effect in the patient. Both the dose and the administration means can be determined based on the specific qualities of the therapeutic, the condition of the patient, the progression of the disease, and other relevant factors. Administration of the therapeutic agents of the invention can include, local or systemic administration, including injection, oral administration, particle gun or catheterized administration, and topical administration. The therapeutics of the invention can be administered in a therapeutically effective dosage and amount, in the process of a therapeutically effective protocol for treatment of the patient. The initial and any subsequent dosages administered will depend upon the patient's age, weight, condition, and the disease, disorder or biological condition being treated. Depending on the therapeutic, the dosage and protocol for administration will vary, and the dosage will also depend on the method of administration selected, for example, local or systemic administration.

For polypeptide therapeutics, for example, a dominant negative mammalian Scm polypeptide or a polypeptide modulator of mammalian Scm, the dosage can be in the range of about 5 $\mu$g to about 50 $\mu$g/kg of patient body weight, also about 50 $\mu$g to about 5 mg/kg, also about 100 $\mu$g to about 500 $\mu$g/kg of patient body weight, and about 200 to about 250 $\mu$g/kg.

For polynucleotide therapeutics, depending on the expression of the polynucleotide in the patient, for tissue targeted administration, vectors containing expressible constructs including mammalian Scm coding sequences or modulator coding sequences, or non-coding sequences can be administered in a range of about 100 ng to about 200 mg of DNA for local administration in a gene therapy protocol, also about 500 ng to about 50 mg, also about 1 ug to about 2 mg of DNA, about 5 ug of DNA to about 500 ug of DNA, and about 20 ug to about 100 ug during a local administration in a gene therapy protocol, and for example, a dosage of about 500 ug, per injection or administration.

Non-coding sequences that act by a catalytic mechanism, for example, catalytically active ribozymes may require lower doses than non-coding sequences that are held to the restrictions of stoichiometry, as in the case of, for example, antisense molecules, although expression limitations of the ribozymes may again raise the dosage requirements of ribozymes being expressed in vivo in order that they achieve efficacy in the patient. Factors such as method of action and efficacy of transformation and expression are therefore considerations that will effect the dosage required for ultimate efficacy for DNA and nucleic acids. Where greater expression is desired, over a larger area of tissue, larger amounts of DNA or the same amounts readministered in a successive protocol of administrations, or several administrations to different adjacent or close tissue portions of for example, a tumor site, may be required to effect a positive therapeutic outcome.

For administration of small molecule modulators of mammalian Scm polypeptide activity, depending on the potency of the small molecule, the dosage may vary. For a very potent inhibitor, microgram ($\mu$g) amounts per kilogram of patient may be sufficient, for example, in the range of about 1 $\mu$g/kg to about 500 mg/kg of patient weight, and about 100 $\mu$g/kg to about 5 mg/kg, and about 1 $\mu$g/kg to about 50 $\mu$g/kg, and, for example, about 10 ug/kg. For administration of peptides and peptoids the potency also affects the dosage, and may be in the range of about 1 $\mu$g/kg to about 500 mg/kg of patient weight, and about 100 $\mu$g/kg to about 5 mg/kg, and about 1 $\mu$g/kg to about 50 $\mu$g/kg, and a usual dose might be about 10 ug/kg.

In all cases, routine experimentation in clinical trials will determine specific ranges for optimal therapeutic effect, for each therapeutic, each administrative protocol, and administration to specific patients will also be adjusted to within effective and safe ranges depending on the patient condition and responsiveness to initial administrations.

Administration of a therapeutic agent for a condition in which increased expression of mammalian Scm is implicated, for example, in the case of promyelocytic leukemia, chronic myelogenous leukemia, lymphoblastic leukemia, Burkitt's lymphoma, colorectal adenocarcinoma, lung carcinoma, melanoma, and lymphoma, can be preceded by diagnosis of the condition using an mammalian Scm probe, generated from any portion of the mammalian Scm gene, and probing the suspect tissue. bDNA technology using bDNA probes to mammalian Scm gene sequences or mammalian Scm mRNA sequences may be used, as described in WO 92/02526 or U.S. Pat. No. 5,451,503, and U.S. Pat. No. 4,775,619.

Once diagnosis is complete, treatment can include administration of mammalian Scm polynucleotides or anti-sense oligonucleotide by a gene therapy protocol, or by administration by other means including local or systemic administration, of an mammalian Scm modulator, for example an mammalian Scm-specific ribozyme, or a genetically altered mammalian Scm variant, for example a dominant negative mammalian Scm, or a small molecule or peptide or peptoid mammalian Scm modulator, or any combination of these potential therapeutics. The patient can be subsequently monitored by periodic reprobing of the affected tissue with an mammalian Scm probe.

Even in cancers where mammalian Scm mutations are not implicated, mammalian Scm upregulation or enhancement of mammalian Scm function may have therapeutic application. In these cancers, increasing mammalian Scm expression or enhancing mammalian Scm function may help to suppress the tumors. Similarly, even in tumors where mammalian Scm expression is not aberrant, effecting mammalian Scm upregulation or augmentation of mammalian Scm activity may suppress metastases.

Further objects, features, and advantages of the present invention will become apparent from the detailed description. It should be understood, however, that the detailed description, while indicating preferred embodiments of the invention, is given by way of illustration only, since various changes and modifications within the spirit and scope of the invention will become apparent to those skilled in the art from this detailed description.

Definitions

A "nucleic acid molecule" or a "polynucleotide," as used herein, refers to either RNA or DNA molecule that encodes a specific amino acid sequence or its complementary strand. Nucleic acid molecules may also be non-coding sequences, for example, a ribozyme, an antisense oligonucleotide, or an untranslated portion of a gene. A "coding sequence" as used herein, refers to either RNA or DNA that encodes a specific amino acid sequence or its complementary strand. A polynucleotide may include, for example, an antisense oligonucleotide, or a ribozyme, and may also include such items as a 3' or 5' untranslated region of a gene, or an intron of a gene, or other region of a gene that does not make up the coding region of the gene. The DNA or RNA may be single stranded or double stranded. Synthetic nucleic acids or synthetic polynucleotides can be chemically synthesized nucleic acid sequences, and may also be modified with chemical moieties to render the molecule resistant to degradation. Synthetic nucleic acids can be ribozymes or antisense molecules, for example. Modifications to synthetic nucleic acid molecules include nucleic acid monomers or derivative or modifications thereof, including chemical moieties. For example, phosphothioates can be used for the modification. A polynucleotide derivative can include, for example, such polynucleotides as branched DNA (bDNA). A polynucleotide can be a synthetic or recombinant polynucleotide, and can be generated, for example, by polymerase chain reaction (PCR) amplification, or recombinant expression of complementary DNA or RNA, or by chemical synthesis. Mammalian Scm polynucleotides contain at least 95% and preferably at least 97% identity to either mouse or human hScm sequences. These can be obtained, inter alia, by hybridization of mouse or human Scm probes under conditions of stringent hybridization. Encompassed within the definition of mammalian, human, and mouse Scm are sequences which contain allelic variants, as well as sequences which differ due to the degeneracy of the genetic code.

The term "functional portion of" as used herein refers to a portion of an mammalian Scm wild-type molecule which retains at least 50% of activity of mammalian Scm. It also encompasses a portion of an mammalian Scmn gene having single base substitutions, deletions, or insertions that have no adverse effect on the activity of the molecule. Truncations of mammalian Scm, fragments of Scm, and combinations of fragments of Scm, which retain at least 50% activity are contemplated. Such portions of hScm may also be fused to other proteins, such as in a gene fusion.

The term "functional" as used herein refers to a gene functional in cancer or differentiation. A molecule is functional if its expression causes, directly or indirectly, an event specifically associated with differentiation, mitosis, oncogenesis, metastasis, or the like.

The term "modulate" as used herein refers to the ability of a molecule to alter the function or expression of another molecule. Thus, modulate could mean, for example, inhibit, antagonize, agonize, upregulate, downregulate, induce, or suppress. A modulator has the capability of altering function of its target. Such alteration can be accomplished at any stage of the transcription, translation, expression or function of the protein, so that, for example, modulation of mammalian Scm can be accomplished by modulation of the DNA, RNA, and protein products of the gene. It assumed that modulation of the function of the target, for example, mammalian Scm, will in turn modulate, alter, or affect the function or pathways leading to a function of genes and proteins that would otherwise associate, and interact, or respond to, mammalian Scm.

A "malignancy" includes any proliferative disorder in which the cells proliferating are ultimately harmful to the host. Cancer is an example of a proliferative disorder that manifests a malignancy. Neoplasia is the state of cells which experience uncontrolled cell growth, whether or not malignant.

The term "regulatory sequence" as used herein refers to a nucleic acid sequence encoding one or more elements that are capable of affecting or effecting expression of a gene sequence, including transcription or translation thereof, when the gene sequence is placed in such a position as to subject it to the control thereof. Such a regulatory sequence can be, for example, a minimal promoter sequence, a complete promoter sequence, an enhancer sequence, an upstream activation sequence ("UAS"), an operator sequence, a downstream termination sequence, a polyadenylation sequence, an optimal 5' leader sequence to optimize initiation of translation, and a Shine-Dalgarno sequence. Alternatively, the regulatory sequence can contain a combination enhancer/promoter element. The regulatory sequence that is appropriate for expression of the present construct differs depending upon the host system in which the construct is to be expressed. Selection of the appropriate regulatory sequences for use herein is within the capability of one skilled in the art. For example, in prokaryotes, such a regulatory sequence can include one or more of a promoter sequence, a ribosomal binding site, and a transcription termination sequence. In eukaryotes, for example, such a sequence can include one or more of a promoter sequence and/or a transcription termination sequence. If any necessary component of a regulatory sequence that is needed for expression is lacking in the polynucleotide construct, such a component can be supplied by a vector into which the polynucleotide construct can be inserted for expression. Regulatory sequences suitable for use herein may be derived from any source including a prokaryotic source, an eukaryotic source, a virus, a viral vector, a bacteriophage or from a linear or circular plasmid. An example of a regulatory sequence is the human immunodeficiency virus ("HIV")

promoter that is located in the U3 and R region of the HIV long terminal repeat ("LTR"). Alternatively, the regulatory sequence herein can be a synthetic sequence, for example, one made by combining the UAS of one gene with the remainder of a requisite promoter from another gene, such as the GADP/ADH2 hybrid promoter.

The terms "protein", "polypeptide", "polypeptide derivatives" and modifications and variants thereof refer herein to the expression product of a polynucleotide construct of the invention as defined above. The terms further include truncations, variants, alleles, analogs and derivatives thereof. Unless specifically mentioned otherwise, such mammalian Scm polypeptides possess one or more of the bioactivities of the mammalian Scm protein, such as those discovered herein. This term is not limited to a specific length of the product of the mammalian Scm gene. Thus, polypeptides that are identical or contain at least 85%, and more preferably 90%, and most preferably 95% identity with the mammalian Scm protein or the mature mammalian Scm protein, wherever derived, from human or nonhuman sources are included within this definition of the mammalian Scm polypeptide. Also included, therefore, are alleles and variants of the product of the mammalian Scm gene that contain amino acid substitutions, deletions, or insertions. The amino acid substitutions can be conservative amino acid substitutions or substitutions to eliminate non-essential amino acid residues such as to alter a glycosylation site, a phosphorylation site, an acetylation site, or to alter the folding pattern by altering the position of the cysteine residue that is not necessary for function, etc. Conservative amino acid substitutions are those that preserve the general charge, hydrophobicity/hydrophilicity and/or steric bulk of the amino acid substituted, for example, substitutions between the members of the following groups are conservative substitutions: Gly/Ala, Val/Ile/Leu, Asp/Glu, Lys/Arg, Asn/Gln, Ser/Thr/Cys and Phe/Trp/Tyr. Analogs include peptides having one or more peptide mimics, also known as peptoids, that possess mammalian Scm protein-like activity. Included within the definition are, for example, polypeptides containing one or more analogs of an amino acid (including, for example, unnatural amino acids, etc.), polypeptides with substituted linkages, as well as other modifications known in the art, both naturally occurring and nonnaturally occurring. The term "mammalian Scm" also may include post-expression modifications of the polypeptide, for example, glycosylations, acetylations, phosphorylations, myrstylations, farnesylations, palmitoylations and the like.

The term "polypeptide fragment" as used herein refers to a polypeptide sequence that does not encode the full length of a protein but that is identical to a region of the protein. The fragment is designed to retain the functional aspect of the region of the polypeptide from which it is derived. Two fragments can cooperate to provide function. Two distinct polypeptide fragments of the same gene may represent expressed splice variants of that gene, although functionality and expression of the polypeptide splice variant products may occur in similar biological conditions, and may be related, at least in part, in function.

The term "derivative" as used herein in reference to a polypeptide or a polynucleotide means a polypeptide or polynucleotide that retains at least 50% of the functionality of the polypeptide or polynucleotide to which it is a derivative. They may be variously modified by nucleotide or amino acid deletions, substitutions, insertions or inversions by, for example, site directed mutagenesis of the underlying nucleic acid molecules. Derivatives of a polypeptide or polynucleotide may also be fragments or combinations of fragments thereof. In any case, a derivative, or a fragment, retains at least some, and preferably all of the function of the polypeptide from which it is derived.

An "isolated polypeptide" or "isolated polynucleotide" as used herein refers to a polypeptide or polynucleotide, respectively, produced in vivo or in vitro in an environment manipulated by humans using state of the art techniques of molecular biology, biochemistry and gene therapy. For example, an isolated polypeptide can be produced in a cell free system by automated peptide or polypeptide synthesis, in heterologous host cells transformed with the nucleic acid sequence encoding the polypeptide and regulatory sequences for expression in the host cells, and in an animal into which the coding sequence of the polypeptide has been introduced for expression in the animal. A polypeptide or polynucleotide is "isolated" for purposes herein to the extent that it is not present in its natural state inside a cell as a product of nature. For example, such isolated polypeptides or polynucleotides can be 10% pure, 20% pure, or a higher degree of purity, such as 50%, 75%, 85%, or 90%.

The term "condition" as used herein in terms of "a patient having a condition" refers to a particular state of molecular and cellular systems in a biological context. A biological context includes any organism considered to have life, and for the purposes of this invention includes but is not limited the following organisms or groups: animals, mammals, humans, and vertebrates. A biological condition can include, for example, a disease or a medical condition that may or may not be characterized by identifiable symptoms or indicators. A "condition characterized by abnormal cell proliferation" is most likely a cancer condition, but may also be a condition arising in the development of an organism.

The term "modulator" as used herein describes any moiety capable of changing the endogenous activity or a polypeptide. Modulatory activities can include, for example, modulation at the level of transcription, translation, expression, secretion, or modulation of polypeptide activity inside or outside a cell. Modulation can include, for example, inhibition, antagonism, and agonism, and modulation can include, for example, modulation of upstream or downstream effects that effect the ultimate activities in a pathway, or modulation of the configuration of a polypeptide such that its activity is altered. Modulation can be transitory or permanent, and may be a dose dependent effect.

The term "inhibitor" for use herein can be any inhibitor of a polypeptide activity. The category includes but is not limited to any of the herein described antagonists of mammalian Scm. The inhibitor of mammalian Scm can be an antibodybased mammalian Scm antagonist, or a polypeptide fragment thereof, a peptide mammalian Scm antagonist, a peptoid mammalian Scm antagonist, or a small molecule mammalian Scm antagonist. The polypeptide inhibitor can be one screened from a cDNA, cRNA, or phage display library of polypeptides. The inhibitor can be a polynucleotide, such as, for example a ribozyme or an antisense oligonucleotide, or can be derivatives of these. It is expected that some inhibitors will act at transcription, some at translation, and some on the mature protein. However, the use and appropriateness of such inhibitors of mammalian Scm for the purposes of the invention are not limited to any theories of mechanism of action of the inhibitor. It is sufficient for purposes of the invention that an inhibitor inhibit the activity of mammalian Scm.

The term "antagonist" as used herein refers to a molecule that inhibits or blocks the activity of a polypeptide, either by blocking the polypeptide itself, or by causing a reduced expression of the polypeptide by either blocking transcription of the gene encoding the polypeptide, or by interfering with or destroying a transcription or translation product of the gene. An antagonist may be, for example, a small molecule, peptide, peptoid, polypeptide, or polynucleotide. The polynucleotide may be, for example, a ribozyme, an antisense oligonucleotide, or a coding sequence.

The term "agonist" as used herein refers to a molecule that mimics the activity of the target polypeptide. For example, in the case of mammalian Scm, an agonist could mimic the transcriptional negative regulation capability of mammalian Scm. An agonist may be, for example a small molecule, peptide, peptoid, polypeptide, or polynucleotide.

The term "pharmaceutical composition" refers to a composition for administration of a therapeutic agent, such as antibodies or a polypeptide, or inhibitors or genes and other therapeutic agents listed herein, in vivo, and refers to any pharmaceutical carrier that does not itself induce the production of antibodies harmful to the individual receiving the composition, and which may be administered without undue toxicity.

The term "an effective amount" as used herein refers to an amount that is effective to induce a desired effect. Where the effect is a therapeutic effect, the effective amount is that amount that will accomplish a therapeutic goal, for example, tumor regression, tumor marker reduction, or a positive indication from other indicia of cancer that indicates a reduction or growth slowing of cancer cells. Where the therapeutic agent is, for example, an antagonist of mammalian Scm, the effective amount of the antagonist would be an amount that antagonizes mammalian Scm activity among a population of cells. The amount that is effective depends in part upon the indicia selected for determining effectiveness, and depends upon the effect sought.

An administration of a therapeutic agent of the invention includes administration of a therapeutically effective amount of the agent of the invention. The term "therapeutically effective amount" as used herein refers to an amount of a therapeutic agent to treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration. Thus, it is not useful to specify an exact effective amount in advance. However, the effective amount for a given situation can be determined by routine experimentation. Administration can include administration of a polypeptide, and causing the polypeptide to be expressed in an animal by administration of the polynucleotide encoding the polypeptide.

A "recombinant vector" herein refers to any vector for transfer or expression of the polynucleotides herein in a cell, including, for example, viral vectors, non-viral vectors, plasmid vectors and vectors derived from the regulatory sequences of heterologous hosts and expression systems.

The term "in vivo administration" refers to administration to a mammal of a polynucleotide encoding a polypeptide for expression in the mammal. In particular, direct in vivo administration involves transfecting a mammal's cell with a coding sequence without removing the cell from the mammal. Thus, direct in vivo administration may include direct injection of the DNA encoding the polypeptide of interest in the region afflicted by the malignancy or proliferative disorder, resulting in expression in the mammal's cells.

The term "ex vivo administration" refers to transfecting a cell, for example, a cell from a population of cells that are malignant or proliferating, after the cell is removed from the mammal. After transfection the cell is then replaced in the mammal. Ex vivo administration can be accomplished by removing cells from a mammal, optionally selecting for cells to transform, (i.e. cells that are malignant or proliferating) rendering the selected cells incapable of replication, transforming the selected cells with a polynucleotide encoding a gene for expression, (i.e. mammalian Scm), including also a regulatory region for facilitating the expression, and placing the transformed cells back into the mammal for expression of the mammalian Scm.

"Biologically active" refers to a molecule that retains a specific activity. A biologically active mammalian Scm polypeptide, for example, retains the activity including for example the control of a homeotic gene or group of homeotic genes.

"Mammalian cell" as used herein refers to a subset of eukaryotic cells useful in the invention as host cells, and includes human cells, and animal cells such as those from dogs, cats, cattle, horses, rabbits, mice, goats, pigs, etc. The cells used can be genetically unaltered or can be genetically altered, for example, by transformation with appropriate expression vectors, marker genes, and the like. Mammalian cells suitable for the method of the invention are any mammalian cell capable of expressing the genes of interest, or any mammalian cells that can express a cDNA library, cRNA library, genomic DNA library or any protein or polypeptide useful in the method of the invention. Mammalian cells also include cells from cell lines such as those immortalized cell lines available from the American Type Culture Collection (ATCC). Such cell lines include, for example, rat pheochromocytoma cells (PC12 cells), embryonal carcinoma cells (P19 cells), Chinese hamster ovary (CHO) cells, HeLa cells, baby hamster kidney (BHK) cells, monkey kidney cells (COS), human hepatocellular carcinoma cells (e.g., Hep G2), human embryonic kidney cells, mouse sertoli cells, canine kidney cells, buffalo rat liver cells, human lung cells, human liver cells, mouse mammary tumor cells, as well as others. Also included are hematopoetic stem cells, neuronal stem cells such as neuronal sphere cells, and embryonic stem cells (ES cells).

The present invention will now be illustrated by reference to the following examples which set forth particularly advantageous embodiments. However, it should be noted that these embodiments are illustrative and are not to be construed as restricting the invention in any way.

EXAMPLE 1

A small molecule modulator of mammalian Scm is identified and incorporated into a pharmaceutical composition including a liposomal-based pharmaceutically acceptable carrier for administration to a cancer patient for controlling the expression or activity of mammalian Scm in the patient. Administration the composition is achieved by injection into the tumor tissue. The patient is monitored for reduction of mammalian Scm activity as a diagnostic marker evaluating the effectiveness of the treatment.

EXAMPLE 2

A population of progenitor cells are treated with a functional portion of recombinant mammalian Scm polypeptide and induced to differentiate. The process is reversed by administering to the population of cells an inhibitor of mammalian Scm activity.

EXAMPLE 3

Northern blots of mRNA isolated from various tissues were probed with mammalian Scm cDNA for an analysis of the expression differential of mammalian Scm in normal and cancerous tissues, using standard techniques for accomplishing the hybridizations. The normal tissues probed were human adult heart, skeletal muscle, pancreas, prostate, testes, ovary, colon, thymus, brain, placenta, lung, liver, kidney, peripheral leukocytes, and spleen. The tissue specific expression of mammalian Scm in normal human adult tissue indicated abundant mammalian Scm transcript in human heart, skeletal muscle, pancreas, and testes. A somewhat less abundant amount of transcript was present in human prostate, ovary, colon, thymus, brain, placenta, lung, liver, and kidney, and the transcript was virtually undetectable in human leukocytes, and undetectable in the human spleen tissue probed.

By contrast, mammalian Scm transcripts were present at an abundantly high level in the following human cancer cell lines: promyelocytic leukemia HL-60, HeLa cell S3, chronic myelogenous leukemia K-562, lymphoblastic leukemia MOLT-4, Burkitt's lymphoma Raji, colorectal adenomcarcinoma SW480, lung carcinoma A549, and melanoma G361. In addition, Scm transcript was also abundantly high in lung carcinoma tissue, colorectal adenocarcinoma tissue, and lymphocytic cancer tissues. The mammalian Scm transcript was approximately 4 to 4.2 kilobases in size for all hybridizations. Hybridizations were conducted using stringent conditions and a standard hybridization protocol for accomplishing Northern blot hybridizations.

Transcript levels were controlled for by probing with actin probe on the same blots probed with mammalian Scm coding sequence.

The description of the invention draws on previously published work and, at times, on pending patent applications. By way of example, such work consists of scientific papers, abstracts, or issued patents, and published patent applications. All published work cited herein are hereby incorporated by reference.

The following sequences are described below:

SEQ ID NOS: 1, 3, and 5 are human cDNA sequences for Scm isoforms

SEQ ID NOS: 2, 4, and 6 are translated human amino acid sequences for the Scm isoforms SEQ ID NO: 7 is the mouse cDNA for Scm SEQ ID NO: 8 is the translated mouse amino acid sequence for Scm

What is claimed is:

1. An isolated nucleic acid molecule which encodes a mammalian Scm polypeptide sequence selected from the group consisting of SEQ ID NO: 2, SEQ ID NO: 4, and SEQ ID NO: 6.

2. An isolated nucleic acid molecule comprising a sequence selected from the group of sequences consisting of SEQ ID NO: 1, SEQ ID NO:3, and SEQ ID NO: 5.

3. A vector comprising the nucleic acid molecule of claim 1.

4. A vector comprising the nucleic acid molecule of claim 2.

* * * * *